United States Patent
Forsell

(10) Patent No.: US 9,724,189 B2
(45) Date of Patent: Aug. 8, 2017

(54) BREAST IMPLANT SYSTEM

(76) Inventor: Peter Forsell, Bouveret (CH)

( * ) Notice: Subject to any disclaimer, the term of this patent is extended or adjusted under 35 U.S.C. 154(b) by 142 days.

(21) Appl. No.: 13/384,471

(22) PCT Filed: Jul. 13, 2010

(86) PCT No.: PCT/EP2010/060078
§ 371 (c)(1),
(2), (4) Date: Jan. 17, 2012

(87) PCT Pub. No.: WO2011/006900
PCT Pub. Date: Jan. 20, 2011

(65) Prior Publication Data
US 2012/0116509 A1    May 10, 2012

Related U.S. Application Data

(60) Provisional application No. 61/213,815, filed on Jul. 17, 2009.

(51) Int. Cl.
*A61F 2/12* (2006.01)

(52) U.S. Cl.
CPC ........ *A61F 2/12* (2013.01); *A61F 2250/0003* (2013.01); *A61F 2250/0004* (2013.01)

(58) Field of Classification Search
CPC ........................................................ A61F 2/12
USPC .................................. 623/7, 8, 23.64–23.68
See application file for complete search history.

(56) References Cited

U.S. PATENT DOCUMENTS

| | | |
|---|---|---|
| 3,683,424 A | 8/1972 | Pangman |
| 4,217,889 A | 8/1980 | Radovan et al. |
| 4,428,082 A * | 1/1984 | Naficy ............................. 623/8 |
| 4,507,810 A | 4/1985 | Bartholdson |
| 4,615,704 A | 10/1986 | Frisch |
| 4,636,213 A | 1/1987 | Pakiam |
| 4,662,357 A | 5/1987 | Pierce et al. |
| 4,731,081 A | 3/1988 | Tiffany et al. |

(Continued)

FOREIGN PATENT DOCUMENTS

| | | |
|---|---|---|
| WO | WO 2006/034273 | 3/2006 |
| WO | WO 2006/079905 A2 | 8/2006 |

(Continued)

OTHER PUBLICATIONS

International Search Report for PCT/EP2010/060078, mailed Sep. 3, 2010.

(Continued)

*Primary Examiner* — Yashita Sharma

(57) ABSTRACT

A breast implant system comprises at least one casing (3, 4) with a flexible outer shape for implantation in a patient's body so as to form part of a breast implant (10) and further comprises at least one first element (1) contained in the casing and optionally at least one second element (2) also contained in the casing. The first and second elements are either displaceable within the casing and/or their volume can be changed in order to change the shape and/or size of the breast implant. A reservoir (R) comprising a lubricating fluid is connected to the casing so as to allow lubricating fluid to be supplied to and removed from the casing in order to reduce surface friction between adjacent elements and/or between the casing and the elements before the shape of the breast implant is changed.

22 Claims, 16 Drawing Sheets

(56) References Cited

U.S. PATENT DOCUMENTS

| | | | |
|---|---|---|---|
| 4,790,848 A * | 12/1988 | Cronin | A61F 2/12 623/8 |
| 4,944,749 A * | 7/1990 | Becker | A61F 2/12 623/8 |
| 4,984,585 A | 1/1991 | Austad | |
| 5,236,454 A | 8/1993 | Miller | |
| 5,246,454 A * | 9/1993 | Peterson | 623/8 |
| 5,549,671 A | 8/1996 | Waybright | |
| 5,779,734 A | 7/1998 | Ledergerber | |
| 5,882,353 A | 3/1999 | Vanbeek et al. | |
| 6,187,043 B1 | 2/2001 | Ledergerber | |
| 6,668,836 B1 | 12/2003 | Greenburg et al. | |
| 6,755,861 B2 | 6/2004 | Nakao | |
| 6,875,233 B1 | 4/2005 | Turner | |
| 7,081,136 B1 | 7/2006 | Becker | |
| 2002/0143396 A1 | 10/2002 | Falcon et al. | |
| 2003/0074084 A1 | 4/2003 | Nakao | |
| 2006/0069403 A1 | 3/2006 | Shalon et al. | |
| 2006/0111791 A1 | 5/2006 | Forsell | |
| 2006/0235482 A1 | 10/2006 | Forsell | |
| 2009/0299473 A1 | 12/2009 | Govin-Yehudian et al. | |
| 2011/0054606 A1 | 3/2011 | Forsell | |
| 2011/0196422 A1 | 8/2011 | Forsell | |

FOREIGN PATENT DOCUMENTS

| | | |
|---|---|---|
| WO | WO 2007/004213 A2 | 1/2007 |
| WO | WO 2008/053630 A1 | 5/2008 |

OTHER PUBLICATIONS

Written Opinion of the International Searching Authority for PCT/EP2010/060078, dated Sep. 3, 2010.
International Search Report for PCT/EP2010/060079, mailed Nov. 23, 2010.
Written Opinion of the International Searching Authority for PCT/EP2010/060079, mailed Nov. 23, 2010.
Written Opinion of the International Searching Authority for PCT/EP2009/000622, mailed Apr. 1, 2009, corresponding to re-lated co-pending U.S. Appl. No. 12/865,306, filed Jul. 29, 2010.
International Search Report issued in corresponding International Application No. PCT/EP2009/000622, mailed Apr. 1, 2009.

* cited by examiner

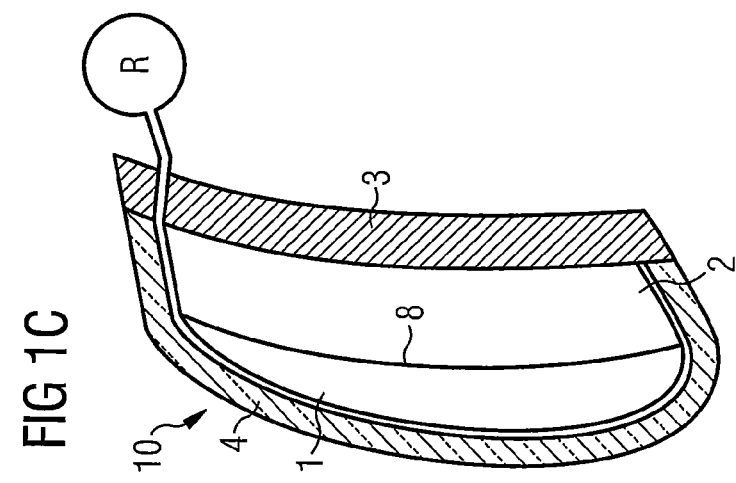
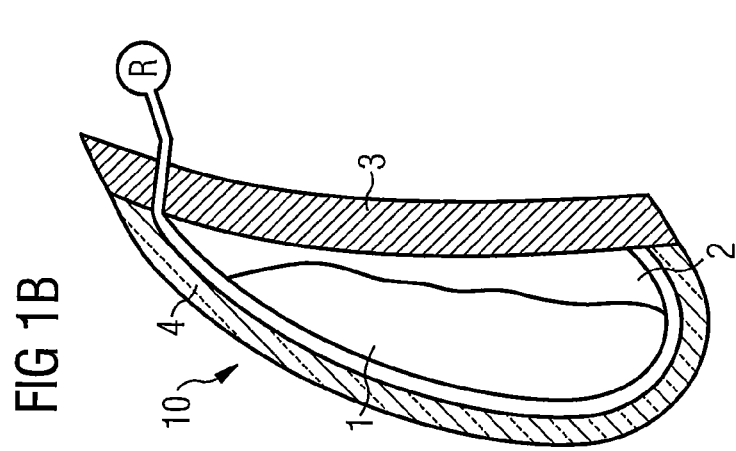
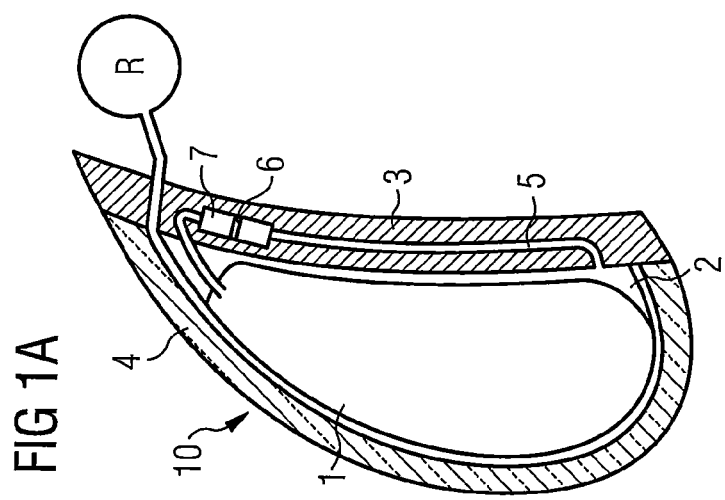

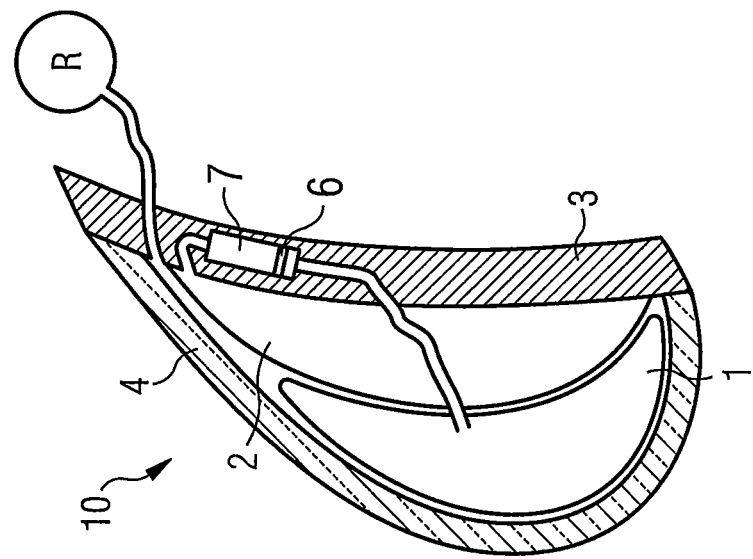
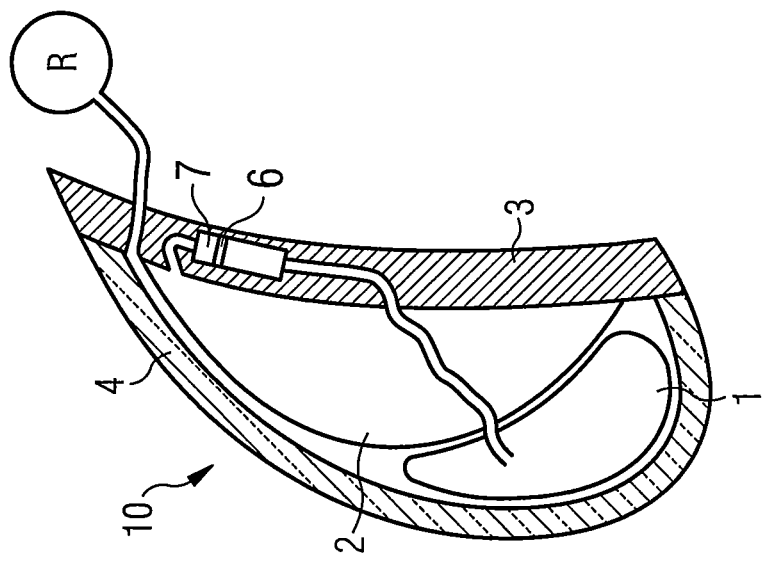

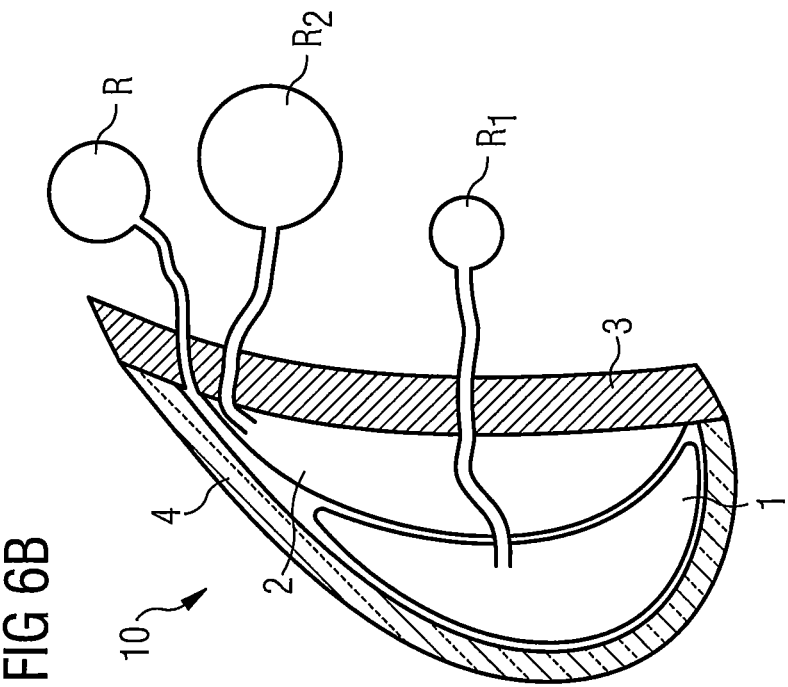
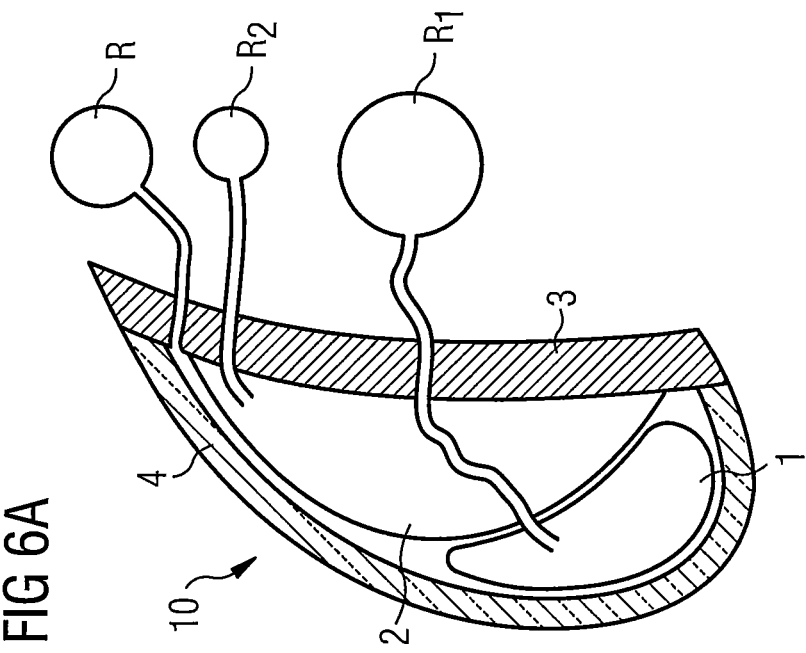

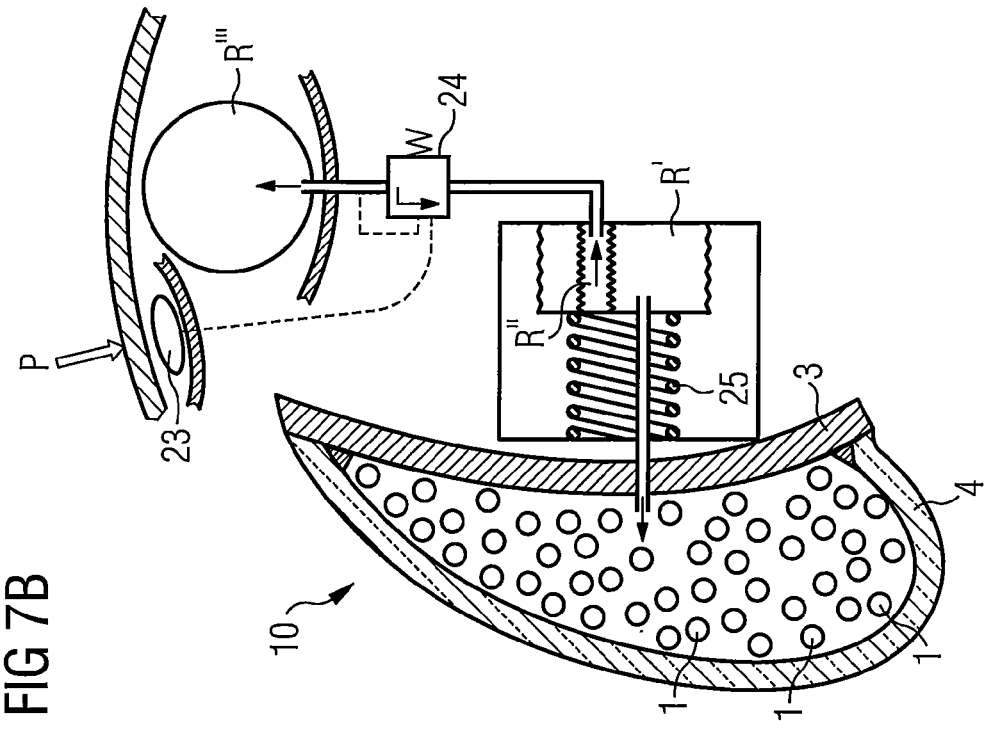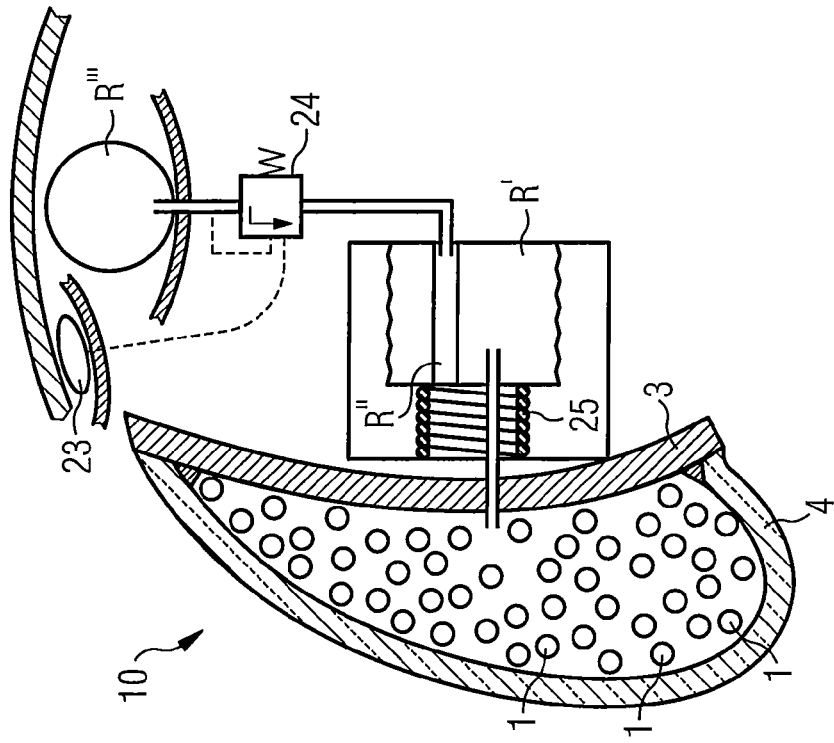

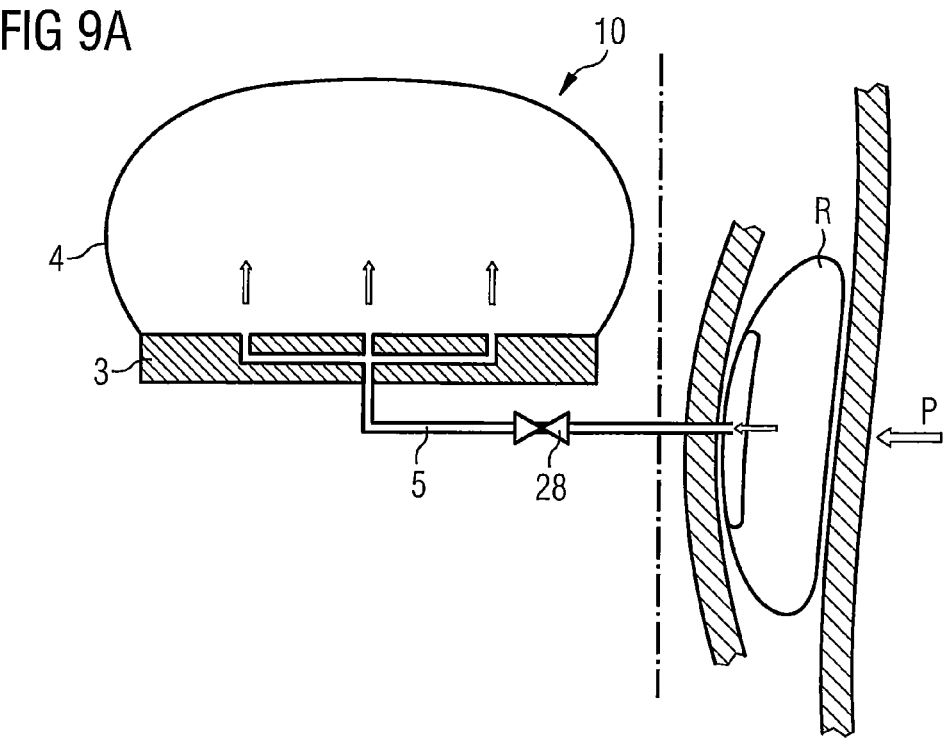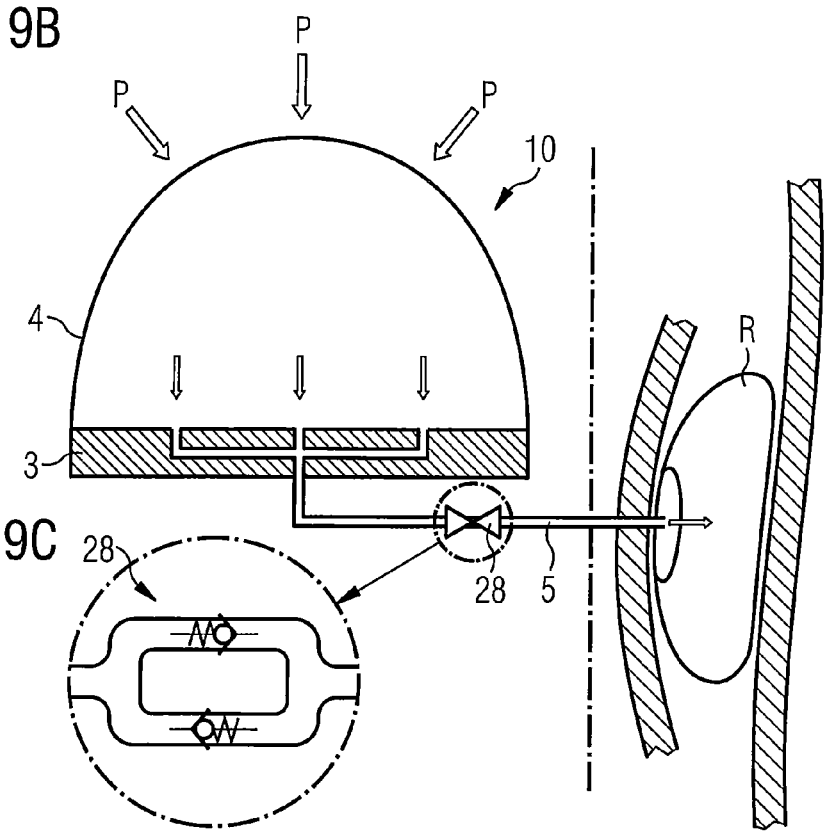

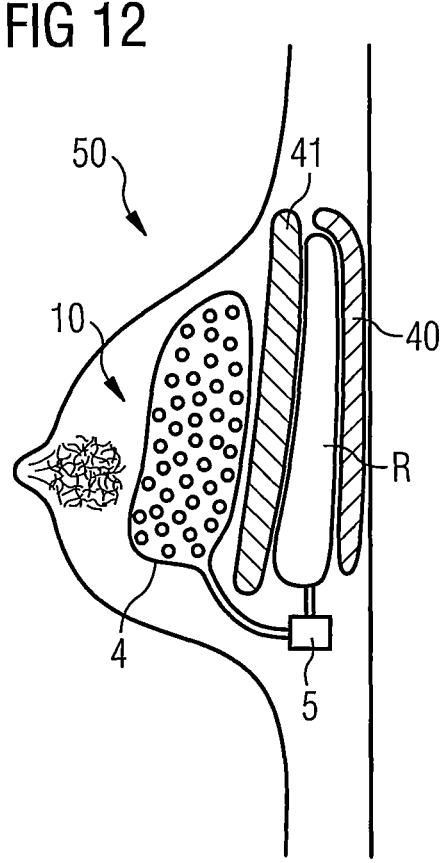

BREAST IMPLANT SYSTEM

This application is the U.S. national phase of International Application No. PCT/EP2010/060078, filed 13 Jul. 2010, which designated the U.S. and claims the benefit of U.S. Provisional No.: 61/213,815, filed 17 Jul. 2009, the entire contents of each of which are hereby incorporated by reference.

BACKGROUND OF THE INVENTION

The present invention relates to a breast implant system which allows the shape of a breast implant to be varied after its implantation in the patient's body. The present invention particularly improves the breast implant system described in international patent application no. PCT/EP2009/000622.

Breast implants are typically used to replace a natural breast that has been removed, e.g. due to cancer, or to increase the size of a natural breast, when the natural size is considered unsatisfactory. In general, people who desire to change the overall size and shape of the breast implants after implantation have to undergo major surgery. It would be desirable for the patient to adjust the size and shape of the breast implant easily, depending on current needs. For instance, as time goes by the patient might no longer be happy with the size or shape of the artificial breast. Or, the patient might want to change the shape or size only temporarily. For instance, one might wish to reduce the volume of the breast implant during sports activities or one might wish to enlarge the size for a particular event, such as a formal evening affair.

U.S. Pat. No. 6,875,233 B1 discloses a breast implant which allows the overall size and shape thereof to be changed once it has been surgically implanted. Such breast implant includes an exterior shell and an inner bladder. The exterior shell is typically a bellows having a plurality of pleats, so that the outer size of the implant is variable. As the bladder is filled, the exterior shell expands in a manner that creates a lifting effect and a ballooning effect. A valve connected to both the exterior shell and the inner bladder can be used to fill the bladder external to the patient without the need for further surgery after the implant has been implanted in the patient. The bladder may be filled with a liquid, a gas or a solid, and such filler can be added and removed through the valve as needed. The valve either remains external, so that it can be used without any further surgery, or it can be located under the patients skin, in which case minor surgery must be performed to access the valve.

The options for changing the shape of this prior art breast implant are limited. Also, it is inconvenient for the patient that the valve for accessing the inner bladder of the breast implant permanently penetrates the patient's skin or, where it is implanted subcutaneously, requires minor surgery to be accessed.

US 2003/0074084 A1 discloses a breast implant with a plurality of chambers. The chambers are differently pressurized in order to control the shape of the breast implant upon inflation thereof. Each chamber may be provided with a pair of conduits for alternatively delivering fluid to and removing fluid from the chamber. Terminal connectors of such conduits can be easily located by medical practitioners for delivery of fluid to or removal of fluid from a desired chamber either manually or assisted by machinery. Alternatively, fluid can be supplied or removed by inserting a hollow needle directly into the chambers of the breast implants.

While the options of changing the shape of this prior art breast implant are improved over the breast implant disclosed in U.S. Pat. No. 6,875,233 B1, a medical practitioner is still needed to achieve different sizes and shapes of the breast implant after its implantation.

In a more simple embodiment described in US 2003/0074084 A1, one-way valves are each disposed between two adjacent chambers for enabling a transfer of fluid from a first to a second of the adjacent chambers upon application of an external compressive force to the first chamber. This way, the valves enable reshaping of the breast implant merely through manipulation. It is even suggested to automatically open and close the valves by wireless remote control.

While this embodiment would allow the shape of the breast implant to be changed non-invasively merely through manipulation, the size of the breast, i.e. the volume of the breast implant would not be affected thereby.

PCT/EP2009/000622 mentioned in the outset also relates to a breast implant system comprising a plurality of chambers which are interconnected when implanted such that fluid can be exchanged between them so as to change their respective fluid content. Various embodiments are disclosed for changing the shape but not the volume, for changing the shape and also the volume without a change of the breast implant's mass (this being achieved by causing a gas-filled chamber to be compressed when liquid is exchanged between chambers of the breast implant), and for changing the shape and also the volume of the breast implant involving a change of the breast implant's mass. It is further described that fluid exchange between the chambers can be achieved by manually compressing the one or the other fluid chamber, similar to the afore-mentioned US 2003/0074084 A1. However, preferred embodiments include a fluid reservoir implanted remote from the breast implant in the patient's abdominal cavity or inside the patient's chest area, such as outside the thorax under the minor pectoralis muscle or between the major and the minor pectoralis muscles. A pump may be provided for pumping the fluid between the chambers of the breast implant and/or between one or more chambers and the remotely implanted reservoir. The pump may be manually driven for which purpose it is advantageously implanted subcutaneously. Alternatively, the pump may be driven by a motor, which may likewise be implanted. Pump and/or motor may be driven by energy wirelessly transmitted from outside the patient's body. A control unit for controlling the entire process, in particular wirelessly, may be further provided. The breast implant may further have a rigid back plate, to which at least one chamber is fixedly connected, to provide stiffness giving the breast implant a basic contour which is maintained throughout any shape changes of the breast implant. Furthermore, in order to improve the overall appearance of the breast implant, the part of the breast implant's outer wall facing away from the patient's chest may comprise a compartment filled with a soft material, such as silicone.

Thus, the breast implant system disclosed in PCT/EP2009/000622 offers a great variety of options for changing the shape and the size of a breast implant after its implantation. The changes can be easily carried out and controlled by the patient without any medical practitioner being involved.

However, with these prior art breast implants the problem arises that upon changing the volume of one or more chambers within the breast implant and, thus, the shape and/or size of the implant, relative movement of mutually adjacent surfaces within the breast implant will occur. More specifically, the outer surface of a first chamber may contact the respective outer surface of a second chamber and/or may contact the afore-mentioned rigid back wall and/or the afore-mentioned flexible outer wall, within which the fluid chambers are held and which may form a silicone-filled compartment as mentioned. Relative movement between the contacting surfaces of one or more of the afore-mentioned elements causes a substantial amount of surface friction which has to be overcome in order to achieve the size and/or shape variation in the desired manner. When the fluid exchange is achieved by locally compressing the breast implant manually or by compressing e.g. a subcutaneously implanted reservoir, the patient has to apply relatively high compressing forces. Where the exchange of fluid is achieved with the aid of an implanted motor, the motor must be relatively strong. In other words, such motor is relatively voluminous and needs much energy, both aspects not being desired for parts to be implanted in a patient's body.

SUMMARY OF THE INVENTION

It is therefore a primary object of the present invention to provide a breast implant or, more specifically, a breast implant system similar to those described before, which allows for easier manipulation of the breast implant when varying the shape and/or size thereof.

A breast implant system according to the present invention comprises a flexible outer casing for implantation in the patient's body which forms part of the breast implant. Such casing may for instance comprise a rigid back plate and/or an outer wall filled with a soft material, as generally known from the afore-mentioned prior art. The breast implant system according to the present invention further comprises at least one first element contained in the casing and may preferably further comprise at least one second element also contained in the casing. In context of the present invention, the term "element" may include a chamber of the type described before, i.e. having a flexible outer wall and being filled with a fluid, in particular a liquid, and being specifically adapted for supplying fluid to and removing fluid from such chamber in order to ultimately change the size and/or shape of the overall breast implant. The term "element" may likewise cover a plurality of permanently interconnected chambers. However, the invention is not limited thereto. It also covers embodiments where the element or elements have a constant volume, i.e. they are not adapted for exchanging fluid content. As such, the content of the chambers need not necessarily be a fluid but may likewise be granular. It is not even necessary that the elements have a flexible outer wall. For instance, a great number of small elements, such as 100 or more, may be contained in the casing of the breast implant system of the present invention. These small elements may or may not be entirely stiff. Thus, independent of the particular constitution of the elements, the elements have in common that they are contained in the casing of the breast implant in order to fill the casing and impart on the casing a particular outer shape which, in turn, defines the outer shape of the breast implant. Thus, by changing the volume of the one or more elements within the casing and/or by rearranging the element or elements within the casing, the shape and/or size of the breast implant will be affected accordingly.

Now, according to the invention, there is further provided a reservoir, which comprises a lubricating fluid. The reservoir is connected to the casing so as to allow the lubricating fluid to be supplied to and removed from the interior of the casing. Surface friction between an outer surface of an element contained in the casing and an adjacent surface of a different element contained in the casing and/or of the casing itself and/or of a different component of the breast implant, such as a rigid back plate, can be reduced by supplying lubricating fluid from the reservoir into the casing.

Thus, when one wishes to change the shape and/or volume of the breast implant, lubricating fluid is first supplied from the reservoir to the casing so that it can flow between contacting surfaces, thereby reducing surface friction. Next, the shape/size of the breast implant is changed in any desired manner, e.g. by manually rearranging the elements contained in the casing from outside the breast implant or by exchanging fluid between elements contained in the casing or between an element in the casing and a remotely implanted reservoir. It should be noted that—although preferred—the invention is not limited to fully implanted breast implant systems, i.e. components thereof may be provided outside the patient's body, such as the lubricating fluid reservoir, the reservoir for fluid exchange with one or more elements contained in the casing, and the like. Once the size/shape of the breast implant has been changed by changing the size and/or the position of one or more element contained in the casing, the lubricating fluid can be removed from the casing so that surface friction of the outer surface of the element or elements will increase. The increased surface friction offers the important advantage that the shape of the breast implant obtained by the manipulation of the element or elements within the casing will substantially be maintained over a long time. This is particularly important in embodiments where the element or elements are not fixedly connected to a supporting structure but are e.g. freely movable within the casing.

Generally, the lubricating fluid may be a liquid or a gas. Where the lubricating fluid is a gas, the casing can be set under gas pressure so as to inflate the casing and thereby facilitate manipulation of the element or elements contained in the casing. However, since it is typically dangerous to handle gas within the human body, the lubricating fluid used in connection with the present invention is preferably a liquid or a gel, in particular an isotonic liquid or gel. The use of an isotonic liquid will not cause any harm to the patient in case of any leakage.

The casing itself has a flexible and preferably also stretchable wall, i.e. an elastic wall, so as to follow any shape changes caused by an internal relocation of the elements. The flexibility or elasticity of the casing's outer wall is also important in respect of fibrosis covering said outer wall, when the breast implant is implanted in the body. The shape of the casing must be sufficiently flexible to allow lengthening of the functional length thereof without interfering with the fibrosis. For instance, the casing's outer wall may have at least one wrinkle or crease, similar to that of a bellows, to allow lengthening of the outer wall without lengthening fibrosis covering the outer wall when implanted.

The breast implant system of the present invention is preferably a fully implantable system (except possibly for a wireless remote control or wireless energy transfer from outside the patient to the implanted system) with no need for medical practitioners to intervene, in particular without any need for surgery, when the size and/or volume of the breast implant is altered. As such, it is preferred to implant the lubricating fluid reservoir within the patient's body along with the breast implant. Since implantation of the breast implant requires surgery in the patient's chest area, the lubrication fluid reservoir may advantageously also be implanted in this area and, more specifically, outside the thorax just like the breast implant. In order not to negatively influence the outer shape of the breast implant, it is preferred that the reservoir is adapted for implantation below the minor pectoralis muscle or between the major and the minor pectoralis muscles.

However, in order to avoid that the lubricating fluid reservoir has any influence on the outer shape of the breast implant, it may be advantageous to adapt the reservoir so that it can be implanted within the patient's body remote from the breast implant, in which case at least one conduit will have to be provided between the remotely implantable reservoir and the casing in order to allow for fluid exchange between them.

Implanting the lubricating fluid reservoir remote from the breast implant may also be advantageous for reasons other than the visual appearance of the breast implant. For instance, the lubricating fluid reservoir may be adapted to be implanted in the armpit or underneath the patient's arm, where it is hidden but can easily be accessed, such as by the patient manually compressing the reservoir and, thus, urging lubricating fluid to flow into the casing.

Alternatively, the lubricating fluid reservoir may be adapted for implantation in the patient's abdominal cavity, because the abdominal cavity generally offers more space for implantation, which is particularly advantageous in case that further components such as a pump and/or a motor and the like are to be implanted along with the reservoir.

It is even possible to implant only a part of the reservoir remote from the breast implant, while another part is implanted as part of the breast implant or next to the breast implant. For instance, where a servo system is used to exchange fluid between the reservoir and the casing, as will be described in more detail below, a first part of the reservoir may be implanted e.g. in the armpit or underneath the patient's arm or in the patient's abdominal cavity in a way to be easily accessible by the patient, in particular subcutaneously, and a more voluminous part of the reservoir may be adapted for implantation somewhere else in the patient's body, i.e. for instance next to the breast implant.

As mentioned before, subcutaneous implantation of at least a part of the reservoir can be made such that manually compressing the subcutaneously implanted part causes fluid to flow from the reservoir into the casing. Advantageously, there is at least one valve provided between the reservoir and the casing restricting flow in the one and/or in the other direction. For instance, a one-way or two-way valve may be provided to prevent lubricating fluid from flowing back to the reservoir while the size and/or shape of the reservoir is being manipulated. Once a desired size/shape has been achieved, the user may compress the breast implant using both hands, thereby increasing the internal pressure in the casing to a value at which the valve opens, and the lubricating fluid will then flow back into the reservoir. Since only a small amount of lubricating fluid is needed to achieve the friction reducing effect, this procedure will not substantially affect the size/shape of the breast implant. Preferably, the valve is a two-way valve which opens towards the casing when the (manual) pressure imparted on the reservoir exceeds a predetermined pressure and opens towards the reservoir when a pressure applied on the casing from outside the breast implant exceeds a predetermined pressure.

In a preferred embodiment, the casing includes 10 or more, hundreds or even thousand or more of small elements, which elements may be granular or spherical, in particular balls. Preferably, these elements should adhere together in the absence of the lubricating fluid. For instance, the elements may be formed as balls not completely filled so that they have a slack outer surface. The contacting surfaces of adjacent balls is, thus, relatively large so that the surface friction resisting relative movement between adjacent balls is likewise relatively large. In the absence of lubricating fluid, the mutual positions of the elements within the casing is unlikely to change substantially over time, whereas the mutual positions of the elements can easily be changed in the presence of the lubricating fluid, e.g. by manual manipulation from outside the breast implant.

It is even within the scope of the present invention that more than one casing is provided in the breast implant. In particular, one or more casings, into which lubricating fluid can be supplied, may be contained within a larger casing, into which the lubricating fluid can likewise be supplied. Thus, the internal casing or casings may constitute "elements" within the larger casing. This way, it is possible to manipulate the elements within the internal casings, which may contain e.g. hundreds of small elements as described above, and to manipulate the internal casings within the larger casing e.g. by rearranging their mutual position within the larger casing.

According to another preferred embodiment of the invention, the element or elements within the casing may have the form of a cushion or pad similar to those typically used for increasing the female breast for aesthetic purposes. Such cushions or pads are filled with a material and have a flexible outer wall, the wall forming the outer surface of the elements. For the reasons already set out before, the flexible outer wall of the cushions or pads are preferably slack so as to increase the contacting surface area and, thus, surface friction with other cushions/pads in the absence of the lubricating fluid.

The filling material of the pad or cushion may be granular but preferably is a soft material, in particular a fluid. As such, the filling material may comprise gas, liquid, gel, foam or any other flowable material, or a combination of the aforementioned materials. Most advantageously, the filling material is a silicone liquid or a silicone gel as the consistency thereof comes closest to that of a natural breast.

As described in the outset, one preferred way of changing the shape and/or size of the breast implant involves fluid to be supplied to and/or removed from at least one of the elements contained in the casing. This can be achieved either by inter-exchanging fluid between at least one first element and at least one second element within the casing. Alternatively, at least one reservoir different from the lubricating fluid reservoir, may be provided in fluid connection with at least one element contained in the casing such that fluid can be exchanged between this (further) reservoir and the respective element.

In the latter case involving the further reservoir, such reservoir may be adapted for implantation below the minor pectoralis muscle or between the major and the minor pectoralis muscles, similar to the lubricating fluid reservoir. It may be placed even further remote from the breast implant in which case, again, at least one conduit will have to be provided for the fluid exchange.

In the former case where fluid is inter-exchanged between first and second elements within the casing, this can be achieved in a simple manner, e.g. by manually compressing the one or the other, thereby urging fluid to flow from the one element into the respective other element. One or more pressure relief valves may be provided between the respective elements, which open at a predetermined pressure. This way, the overall structure can be held relatively simple. More advantageously, the pressure relief valve is a two-way pressure relief valve which opens in the one direction or the other direction depending upon the side where the predetermined pressure is applied.

Instead of inter-exchanging fluid directly between the first and second elements, an intermediate reservoir may be interposed between the two elements such that fluid can be exchanged between the intermediate reservoir and the first and second elements so as to change their respective content. In other words, fluid squeezed out of one element into the intermediate reservoir will cause an equivalent amount of fluid to be urged from the intermediate reservoir into the respective other element. The intermediate reservoir may be arranged e.g. in a rigid back plate of the breast implant which will be described in further detail below.

As in the prior art breast implant systems, the present invention is useful in connection with breast implants having a constant volume and a variable shape, breast implants having a variable volume and a variable shape, and breast implants having a variable volume and shape, but a constant mass.

While in the prior art breast implant systems there is provided a plurality of chambers with variable size and shape, these chambers are arranged in fixed relative positions. More specifically, adjacent chambers are separated by an intermediate wall forming part of both chambers, there being no relative movement between these chambers. In particular, there is no surface friction between outer walls of adjacent chambers. Surface friction mainly occurs between the outer walls of the chambers and a flexible outer wall (casing) within which the chambers of the prior art breast implants may be contained.

According to a preferred embodiment of the present invention, there are provided at least two elements within the casing, of which at least the first element is displaceable relative to the second element by moving the first element between different spots within the casing when the outer shape of the breast implant is to be changed. In other words, an outer surface of the first element being moved from a first spot to a second spot within the casing will be displaced relative to a contacting outer surface of the respective second element contained in the casing.

This opens more flexibility for varying the shape of the breast implant. The area of the outer surface of the one (first) element contacting the other (second) element should be large so that surface friction forces are high in the absence of lubricating fluid and the shape of the breast implant is unlikely to change unintentionally.

The second element, which may form a cushion or pad and which may or may not be interconnected with the first element to allow fluid to be inter-exchanged, may be stationary mounted within the casing. For instance, the second element may form part of the wall of the casing, or more preferably part of a rigid back plate of the breast implant. It is particularly advantageous to stationary mount the second element within the casing when the first and second elements are somehow interconnected in a manner which limits their relative movement. By mounting the second element stationary to the casing, predetermined shapes of the breast implant are easy to obtain, because only the first element needs to be displaced and the displacement can only occur within a predetermined range due to the first element being connected to the stationary mounted second element.

On the other hand, both the first and second elements may each be arranged within the casing so as to be movable between different spots. This arrangement offers maximum flexibility for any shape changes. But also in this case can it be advantageous to interconnect the first and second elements so as to limit their relative displaceability.

According to another embodiment, either or both of the first and second elements are mounted within the casing so as to be movable only between predetermined spots. Thus, the respective element is not stationary mounted within the casing but there is a range of spots between which it can be moved. This allows a general structure to be maintained while permitting certain changes to be made within such structure.

It is even possible to stationary mount the second element to a wall of the casing and to mount the first element so as to be movable within the casing only between predetermined spots. For instance, the first element may be somehow connected to the second element or may be connected somehow to a wall of the casing, or both. With this arrangement, it is possible to provide a structure in which one or more first element is movable from a spot located at least partly beside the second element (which can likewise be said to be a spot above or below the second element, depending upon the perspective) to a spot on top of the second element so as to change the outer shape of the breast implant from relatively flat to relatively high.

Of course, it is also possible to provide each of the first and second elements within the casing so as to be entirely freely movable therein.

The very purpose is in each case to change the outer shape of the breast implant post-operatively and, in particular, non-invasively.

As mentioned before, the breast implant preferably has a rigid back wall arranged to being placed adjacent the patient's thorax. The back wall provides stiffness and gives the breast implant a basic contour which is maintained throughout any shape changes of the breast implant. The rigid back wall advantageously forms part of the casing.

In addition to or independent from any rigid back wall, the casing may have a structure comprising at least one compartment filled with a soft material such as a foam or silicone. This gives the breast implant the look and feel of a natural breast and can also serve to level out any unevenness caused by different fillings and/or different pressures in the elements contained in the breast implant's casing or caused by an uneven distribution of the elements within the casing.

It has already been mentioned before that the use of a servo system may facilitate the exchange of fluid between the lubricating fluid reservoir and the casing (and likewise between a "further" reservoir and one or more of the elements contained in the casing). A servo system in the sense of the present invention is to be understood as a system in which an amount of fluid is displaced between sub-chambers of the lubricating fluid reservoir, which amount is different to the amount of fluid exchanged between the lubricating fluid reservoir and the casing (or the "further" reservoir and one or more of the elements contained in the casing).

There are various alternative ways of realizing such servo system in the breast implant system of the present invention. In this context, it is preferable to provide a spring element to urge the lubricating fluid reservoir or at least one of the sub-chambers thereof into a state of minimum or maximum volume, i.e. into a normally small or a normally large state. Energy, such as a manual compressing force on a subcutaneously implanted sub-chamber, is then only needed to exchange fluid between the casing and the reservoir in one direction, whereas the necessary force required to exchange the fluid in the opposite direction is provided by the spring force. In the same manner, fluid can be exchanged between a further reservoir and one or more elements contained in the casing in order to change the size and/or shape of the breast implant.

The servo system can be designed as a reverse servo system to the extent that only a little amount of fluid needs to be exchanged between the sub-chambers of the reservoir in order to achieve a relatively large amount of fluid exchange between the reservoir and the casing. This means that a relatively large force but small stroke is needed to achieve the relatively large amount of fluid exchange between the reservoir and the casing. This is particularly convenient where one of the sub-chambers of the reservoir is provided for subcutaneous implantation so as to be manually compressible by the patient from outside the patient's body. Thus, the subcutaneously arranged compressible sub-chamber may have a relatively small volume and will therefore not adversely affect the patients visual appearance, however, with the negative side effect that the patient will have to apply a relatively large force to the relatively small subcutaneous sub-chamber in order to achieve the desired, relatively large fluid exchange. Such sub-chamber can be placed advantageously under the patient's arm.

After a while it may become necessary to add lubricating fluid to the reservoir or to add to a further reservoir fluid used for inflating and deflating one or more elements contained in the casing. In particular, when gas is contained in one or another reservoir, it is possible that part of the gas will escape over time due to leakage. Therefore, in order to maintain a desired balance in the reservoir or reservoirs, the breast implant system according to a preferred embodiment includes at least one injection port for implantation under the patient's skin so as to allow fluid to be added to or removed from any reservoir by injection from outside the patient's body. Thus, the injection port is primarily provided for calibrating purposes. Preferably, the system is adapted to maintain shape and size of the breast implant while fluid is added to or removed from the reservoir via said injection port. Then, after fluid has been added or withdrawn from said injection port, the breast implant is adapted to change shape or size to a larger or lesser extent in a calibration procedure.

The injection port or ports can further be used to adjust the pressure in the breast implant system. For instance, when a patient has achieved a particular distribution of fluid among fluid-filled elements contained in the casing, it is convenient for the patient to release any excess pressure from the system by selectively removing fluid from the system through the injection port or ports.

As mentioned in the outset, a pump may be provided in the breast implant system for exchanging lubricating fluid between the reservoir and the casing. The same pump or a different pump may likewise be used for pumping fluid between fluid-filled elements contained in the casing or for pumping fluid into and out of one or more fluid-filled elements contained in the casing. The further reservoir may alternatively be connected to the pump so as to allow for fluid exchange between fluid-filled elements in the casing by pumping fluid with said pump from a first element into the further reservoir and from the further reservoir into the second element, and vice versa.

The pump or pumps may be adapted for implantation under the patient's skin so as to be manually operable through the skin. In this case, a purely hydraulic or purely pneumatic pump may be used.

However, where the pump is not manually operable, the breast implant system may comprise at least one motor for automatically driving the pump. In this case, the pump may be of the hydraulic, pneumatic or mechanical type. Also, a manually operable switch for activating the motor may be arranged subcutaneously for operation by the patient from outside the patient's body.

The motor itself may be arranged to be driven by electric or electromagnetic energy, by an electric or magnetic pulsating field or by ultrasonic energy.

The breast implant system may further comprise an energy source for supplying the energy directly or indirectly to at least one energy consuming part of the system, in particular to the aforementioned motor for driving the pump. Such energy source may include energy storage means, such as a battery or an accumulator, in particular one or more of a rechargeable battery and a capacitor.

The energy source, when provided outside the patient's body, preferably comprises a wireless energy transmitter for wirelessly transmitting energy from outside the patient's body directly or indirectly to the energy consuming part or to an implanted energy storage means.

The breast implant system preferably further comprises an implantable energy transforming device for transforming wirelessly transmitted energy into electric energy. The electric energy is stored in the energy storage means and/or is used to drive the energy consuming part, such as the motor and the pump, as the energy transforming device transforms the wireless energy into the electric energy. Alternatively, the energy consuming part may be adapted to directly transform the wirelessly transmitted energy into kinetic energy.

It is further preferred to provide the breast implant system with a control unit to directly or indirectly control one or more elements of the breast implant system, in particular the pump and the motor. For instance, the control unit may be primarily adapted to control the exchange of lubricating fluid between the reservoir and the casing and/or to control fluid flow into or out of or between one or more elements contained in the casing. Preferably, such controlling action is carried out non-invasively from outside the patient's body, such as by wireless remote control. In this case, a part of the control unit is implanted in the patient's body, whereas another part is not implanted. In particular in the case where the control unit is completely implanted in the patient's body, a manually operable switch for activating the control unit may be arranged subcutaneously so as to be operable from outside the patient's body.

Where one part of the control unit is provided outside the patient's body and the other part is implanted in the patient's body, the external part of the control unit may be used to program the implanted part of the control unit, preferably wirelessly. Also, the implantable part of the control unit may be adapted to transmit feed-back signals to the external part of the control unit. Such signals may relate to functional and/or physical parameters of the system and/or patient and/or may relate to the energy stored in the energy storage means and/or to an energy balance of the system.

The invention will now be described in more detail in context with some preferred embodiments of the invention as shown in the accompanying drawings.

BRIEF DESCRIPTION OF THE DRAWINGS

FIGS. 1A-1C show a breast implant system according to a first embodiment of the invention, FIGS. 5A-5F show a breast implant system according to a fifth embodiment of the present invention, FIGS. 6A-6B show a breast implant system according to a sixth embodiment of the present invention, FIGS. 7A-7D show a breast implant system according to a seventh embodiment of the present invention, FIGS. 9A-9C show a breast implant system according to a ninth embodiment of the present invention, FIGS. 11A-11D show a breast implant system according to an eleventh embodiment of the invention and FIG. 12 shows a breast implant system according to a twelfth embodiment of the invention.

DETAILED DESCRIPTION OF PREFERRED EMBODIMENTS

Figure 2A:
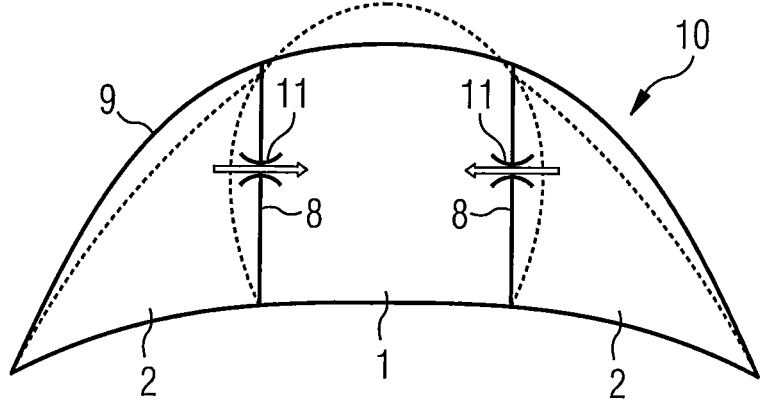
FIGS. 2A-2C show a breast implant system according to a second embodiment of the present invention.

FIG. 1A shows very schematically a vertical cross-sectional view of a breast implant system according to a first embodiment. The breast implant system comprises a first fluid chamber 1 and a second fluid chamber 2, each forming part of the breast implant 10 to be implanted in the breast area of a patient. The first and second fluid chambers 1, 2 are fixedly mounted to a rigid back plate 3 with a contour adapted to be placed adjacent to the patients thorax. The rigid back plate 3 and a flexible outer wall 4 together form a casing within which the first and second fluid chambers 1, 2 are contained. A fluid line 5 connects the first and second fluid chambers 1, 2 and runs, in the embodiment shown, through the rigid back plate 3. A pump is included in the fluid line 5 and is shown only very schematically. The pump can have many different forms and can be of any suitable type. Instead of incorporating the pump in the rigid back wall 3, it may likewise be adapted for implantation remote from the breast implant 10, i.e. in an area with less space constraints. Also, the actual manner of driving the pump, such as manually or automatically by means of a motor, is of no particular importance here and can be chosen appropriately. In the embodiment shown, the pump includes a piston 6 movable in a reservoir 7, the one end of which being connected via the fluid line 5 to the first fluid chamber 1 and the other end of which being connected via the fluid line 5 to the second fluid chamber 2. Using the movable piston, fluid can be pumped and, thus, exchanged between the first and second fluid chambers 1 and 2.

In FIG. 1A the fluid chamber 1 is filled with fluid almost to its maximum capacity, so that the overall breast implant 10 is relatively sturdy. FIG. 1B shows the same breast implant 10 with some fluid being removed from the first fluid chamber 1 to the second fluid chamber 2 using the pump (not shown in FIG. 1B). In this state, the breast implant 10 is relatively flaccid. FIG. 1C shows the same breast implant with the second fluid chamber 2 being filled almost to its maximum. The volume of the fluid chamber 1 is accordingly decreased. In this case, again, the breast implant is relatively sturdy and is lifted more above the rigid back plate 3 as compared to the state shown in FIG. 1A. The sturdiness of the breast implant 10 in the stage shown in FIG. 1C results partly from the fact that a pressure will build up in the second fluid chamber 2 as the volume of the second fluid chamber 2 reaches its maximum capacity.

In the state shown in FIG. 1B the tension within the outer wall of the first and second fluid chambers 1, 2 is negligible. This may cause the outer wall to assume a position within the casing 3, 4 which is not ideal when at a later time a change of the shape of the breast implant is desired by inter-exchanging fluid between the fluid chambers 1, 2. That is, the outer surface of the fluid chambers 1, 2 might need displacement relative to the inner surface of the casing 3, 4. Surface friction forces will have to be overcome in such case. In order to temporarily reduce the surface friction, a reservoir R containing a lubricating fluid, such as an isotonic liquid, is connected to the interior of the casing at a position between an outer wall of the fluid chambers 1, 2 and an inner surface of the casing 3, 4. Before moving fluid from fluid chamber 1 to fluid chamber 2, lubricating fluid from reservoir R is supplied into the casing to reduce the surface friction. When the shape of the breast implant is changed from a state shown in FIG. 1A to the state shown in FIG. 1C, the breast implant undergoes an intermediate state shown in FIG. 1B. Thus, the lubricating fluid reservoir R is shown in FIG. 1B with a smaller volume as compared to FIGS. 1A and 1C, since part of its volume has been displaced into the casing 3, 4 in order to reduce surface friction. Once the state shown in FIG. 1C is reached, the lubricating fluid can be removed from the casing 4 back into the reservoir R.

FIG. 2A shows a simplified structure of a cross-sectional view through a breast implant according to a second embodiment. Unlike FIG. 1, FIG. 2A shows a cross-section taken horizontally through the breast implant and, furthermore, the rigid back plate. The casing 3, 4 and the lubricating fluid reservoir R are not shown here for reasons of simplification, but are likewise present. The breast implant 10 of FIG. 2A comprises one first fluid chamber 1 and two second fluid chambers 2.

More fluid chambers 1 and more or fewer fluid chambers 2 can also be present. In this embodiment, the fluid chambers 1 and 2 are separated by separating walls 8 made from a polymer material. The separating walls 8 are flexible, but preferably non-stretchable. The outer wall of the fluid chambers 1, 2 is also flexible and preferably stretchable. Thus, it is likewise possible in this embodiment that surface friction between the fluid chambers' outer walls and the casing's 3, 4 inner wall generate surface friction forces which can be reduced by means of lubricating fluid as described before.

Valves 11 are provided in the separating walls 8 to allow fluid to be exchanged between the fluid chambers 1, 2. These valves 11 are designed as pressure relief valves and can be of many different types. The purpose of the valves 11 is to allow fluid to flow from one fluid chamber to the next fluid chamber when a predetermined pressure difference is exceeded. In order to allow fluid to flow through the same valve in both directions, the valves 11 are formed as two-way pressure relief valves. A very simple way of providing such two-way pressure relief valve is shown in FIG. 2C. Accordingly, there is a slit 12 in the flexible separating wall 8 which opens when a certain pressure difference between the adjacent fluid chambers is exceeded. FIG. 2A shows a "medium" state of the breast implant 10. However, FIG. 2A also shows by dotted lines one possible extreme state of the breast implant 10. That is, when the pressure in the second fluid chambers 2 is increased, such as by the patient manually compressing the second fluid chambers 2, fluid will flow into the first fluid chamber 1, as shown by the arrows. Then, when the patient releases the pressure on the second fluid chambers 2, the breast implant 10 will assume the shape as shown by the dotted lines.

Figure 2B:
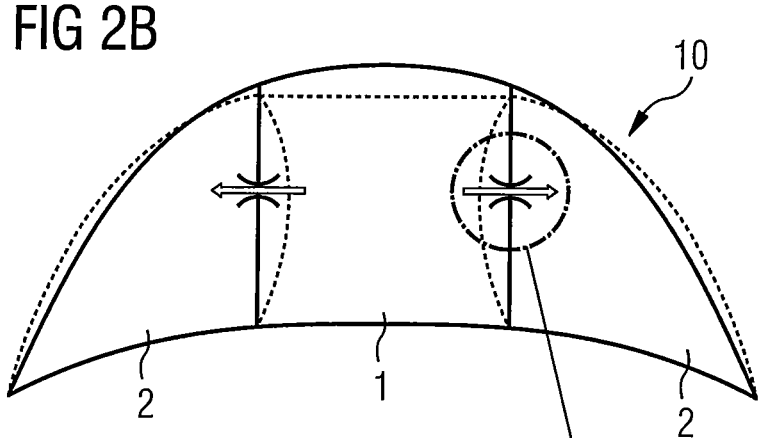
Figure 2C:
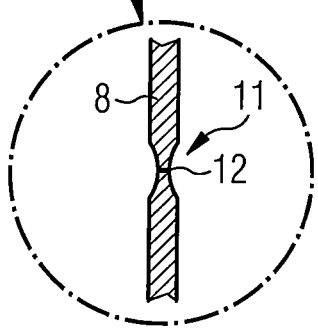

FIG. 2B shows in dotted lines another extreme state of the breast implant 10 of FIG. 2A. In this case, when the pressure in the first fluid chamber 1 is increased, fluid is made to flow into the adjacent second fluid chambers 2 as indicated in FIG. 2B by the arrows. Once the pressure is released, the breast implant 10 will take the shape as shown in FIG. 2B by the dotted lines. Accordingly, the patient can easily change the shape of the breast implant 10 between the three states shown in FIGS. 2A and 2B. Additional intermediate states can also be achieved and even other forms can be achieved, for instance when only one of the two second fluid chambers 2 is compressed to urge fluid into the neighboring first fluid chamber 1.

Figure 3A:
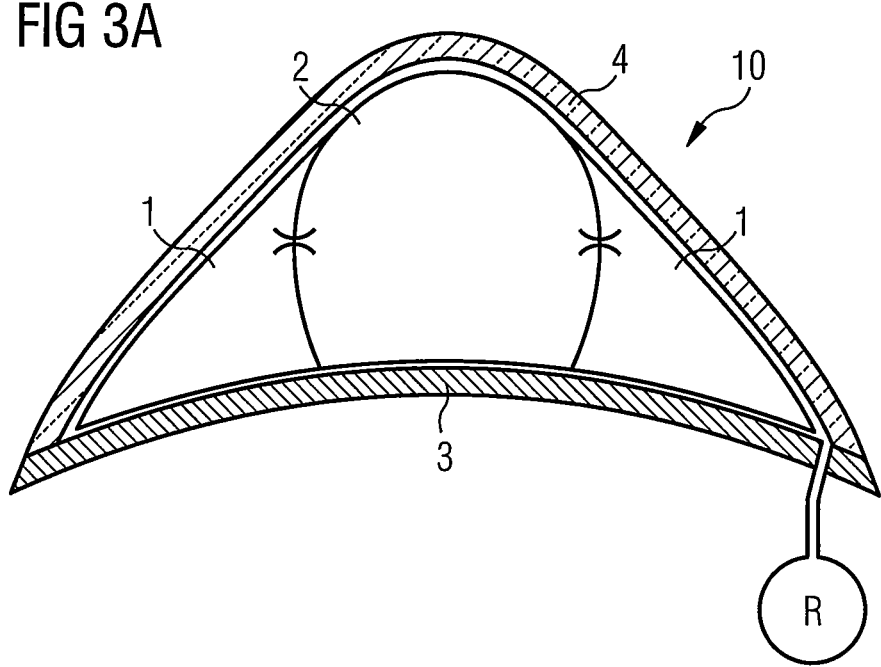
FIGS. 3A-3B show a breast implant system according to a third embodiment of the present invention.
Figure 3B:
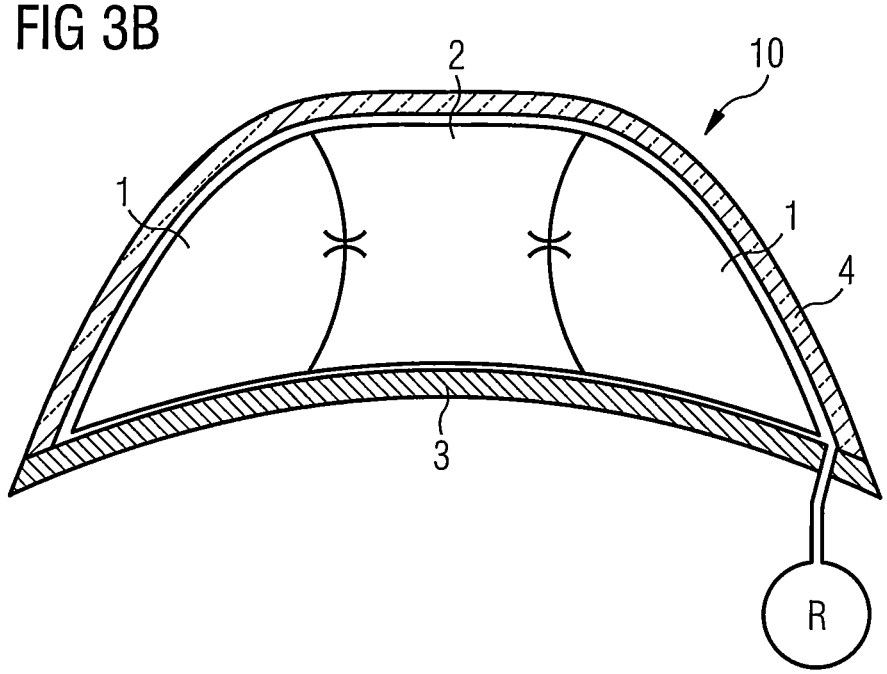

FIGS. 3A and 3B show the breast implant 10 of FIGS. 2A, 2B contained in a casing 4 which, again, is constituted in the embodiment shown by rigid back plate 3 and outer wall 4. The outer wall 4 may be filled with a liquid or gel type silicone or with a foam or a combination thereof. Also, bubbles of air or collagen may be incorporated in the silicone, foam or other soft material. The compartment forming the outer wall 4 is completely separate from the interconnected first and second chambers 1, 2. FIGS. 3A and 3B demonstrate how the outer wall can level out irregularities of the breast implant's outer shape. More importantly, however, the outer wall 4 forms a barrier between the flexible, stretchable inner fluid chambers 1, 2 and any fibrosis that might form on the outside of the breast implant and, further, forms a barrier for the lubricating fluid introduced into the casing from the reservoir R.

Figure 4A:
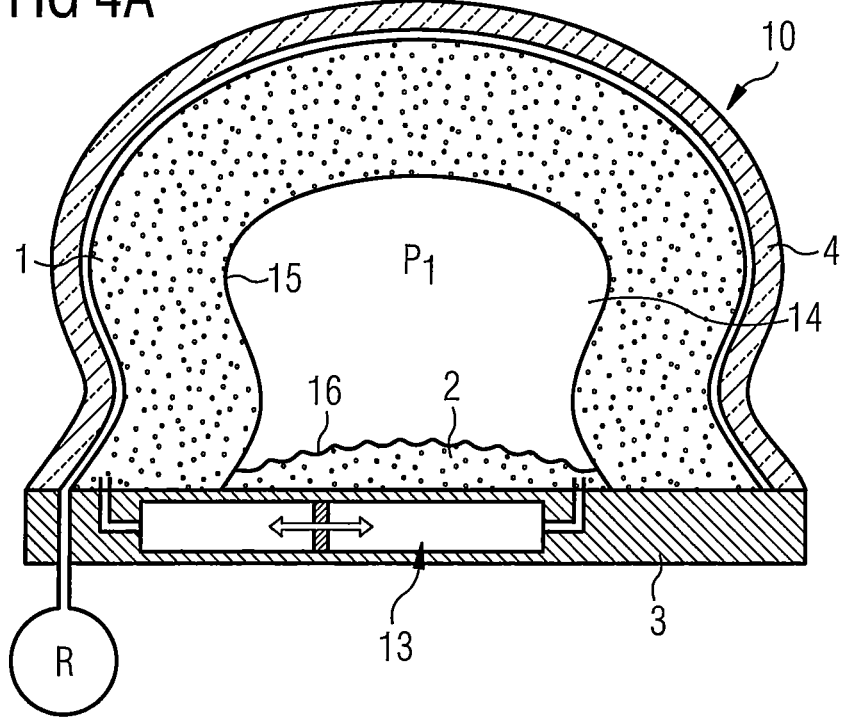
FIGS. 4A-4B show a breast implant system according to a fourth embodiment of the present invention.
Figure 4B:
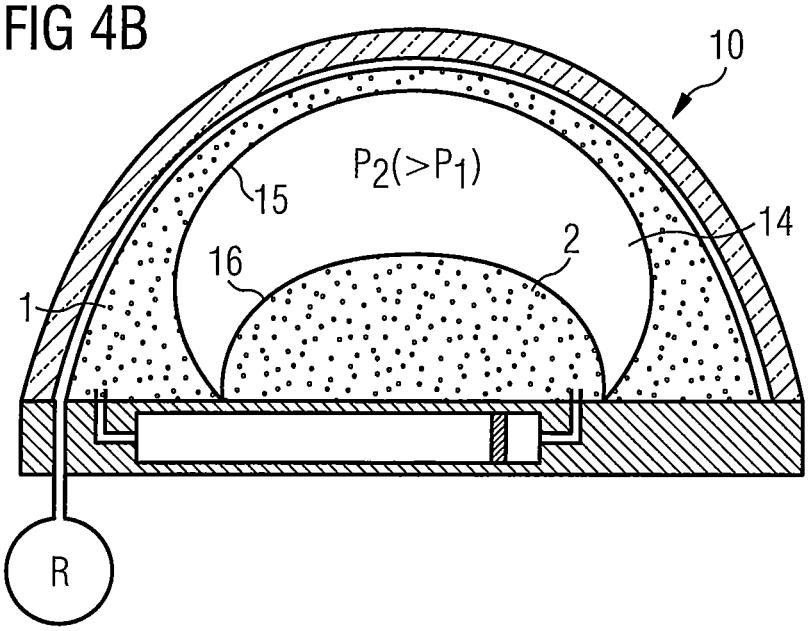

FIGS. 4A and 4B show a fourth embodiment of a breast implant. Again, a rigid back plate 3 and a wall 4 together form a casing, in which a first fluid chamber 1 and a second fluid chamber 2 are arranged. The first and second fluid chambers 1, 2 are fixedly mounted to the rigid back plate 3. By means of a pump generally designated here with reference numeral 13 and again integrated in the rigid back plate 3 in the embodiment shown, fluid can be exchanged between the first and second fluid chambers 1, 2. The first fluid chamber 1 together with the back plate 3 defines an enclosed space forming a third fluid chamber 14. The third fluid chamber 14 comprises a compressible medium, such as a gas or a foam in which the gas is contained. Fluid is exchanged only between the first and second chambers 1, 2, whereas the third fluid chamber 14 is completely isolated, being separated from the first fluid chamber by separating wall 15 and from the second fluid chamber 2 by separating wall 16. Both separating walls 15, 16 are flexible and at least the separating wall 15 should be non-stretchable.

When fluid is pumped from the first fluid chamber 1 into the second fluid chamber 2, the volumes of the fluid chambers 1 and 2 will change accordingly, as is shown in FIG. 4B. The wall of the first fluid chamber 1 is elastic—in the embodiment shown—so as to adapt to the reduced volume, but may also be non-elastic, provided that it is sufficiently flexible to conform with the changed volume. The outer wall 4 forming part of the casing should likewise be stretchable to conform to changed shapes and volumes, and may generally have the same structure as the outer wall 4 shown in the previous embodiments (and in all embodiments described hereinafter). Due to the fact that the separating wall 15 is non-stretchable, the increased volume of the second fluid chamber 2 causes the pressure in the third fluid chamber 14 to rise from an initial pressure P1 to a raised pressure P2. Altogether not only has the shape of the breast implant 10 dramatically changed, but the volume has also changed. However, the mass and, thus, the weight of the breast implant has not changed at all.

While FIGS. 1 to 3 relate to breast implants with constant volume and weight but variable shape, and FIG. 4 relates to an embodiment with a constant weight but variable shape and volume, the following embodiments relate to breast implants where the variable shape and volume involves a weight change of the breast implant. Furthermore, unlike the previous embodiments where the fluid chambers 1, 2 were attached to each other and to the casing, in the following embodiments at least one of the elements contained in the casing for changing the shape/volume of the breast implant can be moved between different spots within the casing so as to change the outer shape of the breast implant.

The breast implant 10 according to a fifth embodiment shown in FIG. 5A to 5D has a casing substantially formed from a rigid back wall 3 and an outer wall 4 fixedly connected thereto. Within the casing 3, 4 a first cushion-like or pad-like element 1 and a second cushion-like or pad-like element 2 are accommodated. Elements 1 and 2 may be similar to the fluid chambers 1, 2 with variable fluid content as described before (see also hereinafter FIG. 5E, 5F and FIG. 6A, 6B). However, it is likewise possible that elements 1, 2 rather have a constant volume and e.g. are filled with granular material or a gel material. In the embodiment shown in FIGS. 5A to 5D, the second element 2 is fixedly mounted to the casing, more exactly to the rigid back plate 3. The first element 1 is to a great extent freely movable within the casing 3, 4.

The breast implant system here includes a servo system for supplying lubricating fluid from the lubricating fluid reservoir into the casing 3, 4. The lubricating fluid reservoir here consists of three sub-chambers R', R", R''', of which only the first sub-chamber R' is in fluid connection with the interior of the casing 3, 4 via fluid line 5. The entire servo system is implanted in the patient's body remote from the breast implant 10. The first sub-chamber R' has the form of a bellows. The second sub-chamber R" cooperates with the first sub-chamber R' such that filling of the second sub-chamber R" with a fluid from the third sub-chamber R''' will cause the first sub-chamber R' to expand, and vice versa. Thus, when fluid is removed from the second sub-chamber R" into the third sub-chamber R''', the length and, thus, the volume of the first sub-chamber R' decreases. The situation is such, however, that the volume change in the second sub-chamber R', which is also in the form of a bellows (see FIG. 5B), is less than the volume change in the first sub-chamber R'.

The way of supplying lubricating fluid from the first sub-chamber R' into the casing 3, 4 will now be explained in relation to FIGS. 5A and 5B. That is, the patient has a subcutaneously arranged pressure chamber 23 in order to open a valve 24 arranged between the second and third sub-chambers R" and R''' of the lubricating fluid reservoir, thereby allowing fluid to flow between the sub-chambers R" and R'''. A preloaded spring 25 will cause the first sub-chamber R' to decrease, thereby urging not only fluid from the second sub-chamber R" to flow to the third sub-chamber R''' but also lubricating fluid from the first sub-chamber R' to flow into the interior of the casing 3, 4 of the breast implant 10. The resulting state of the breast implant system is shown in FIG. 5B.

Figure 5A:
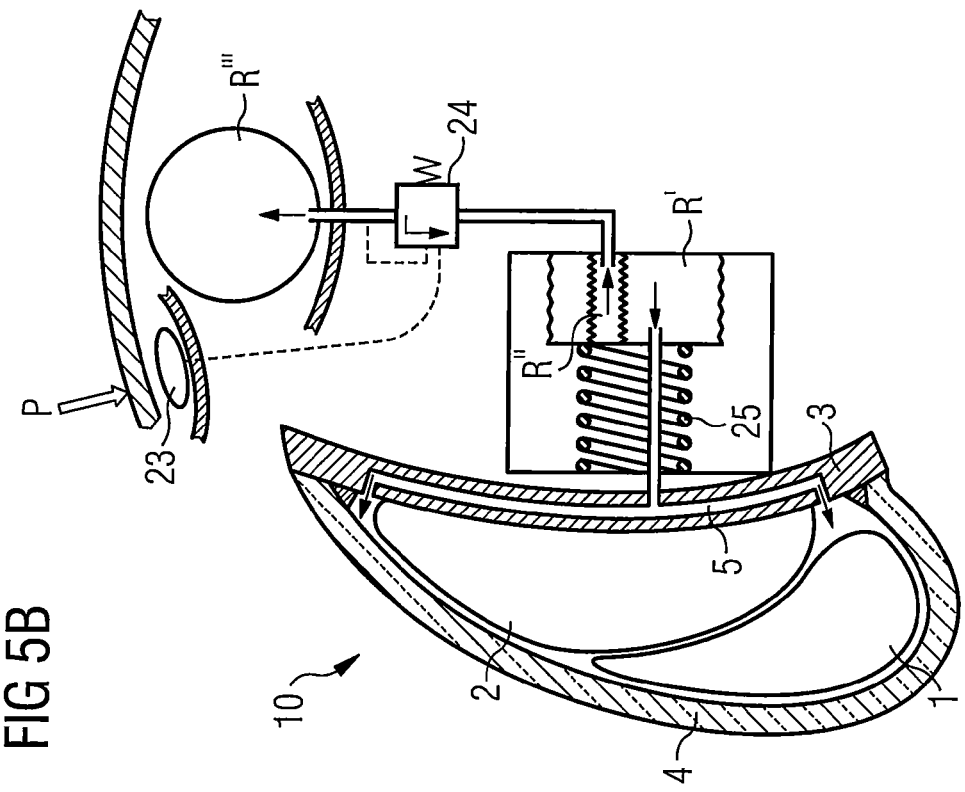
Figure 5B:
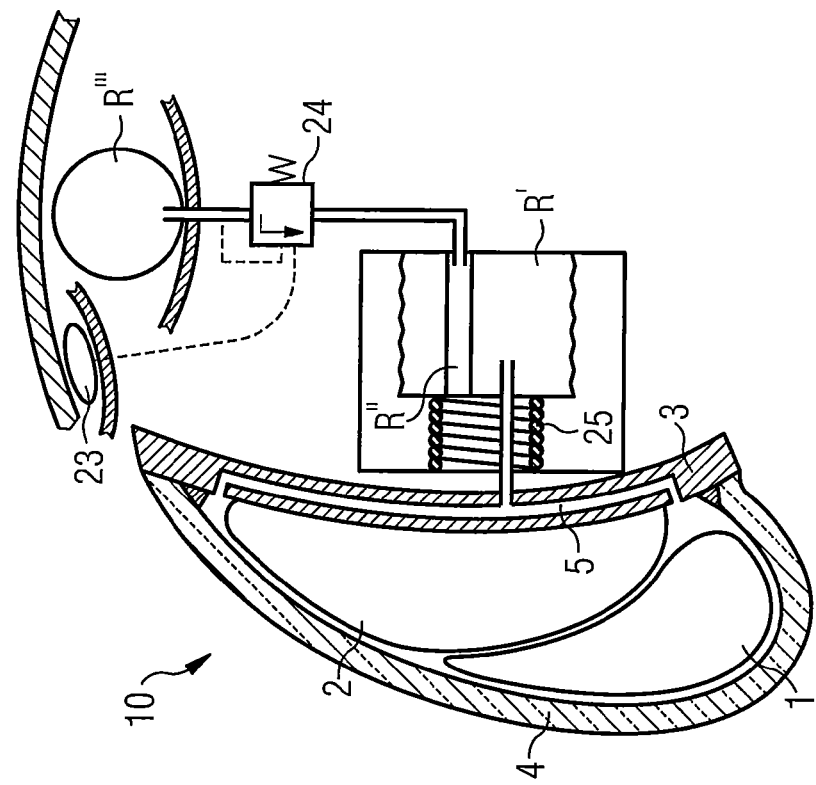
Figure 5C:
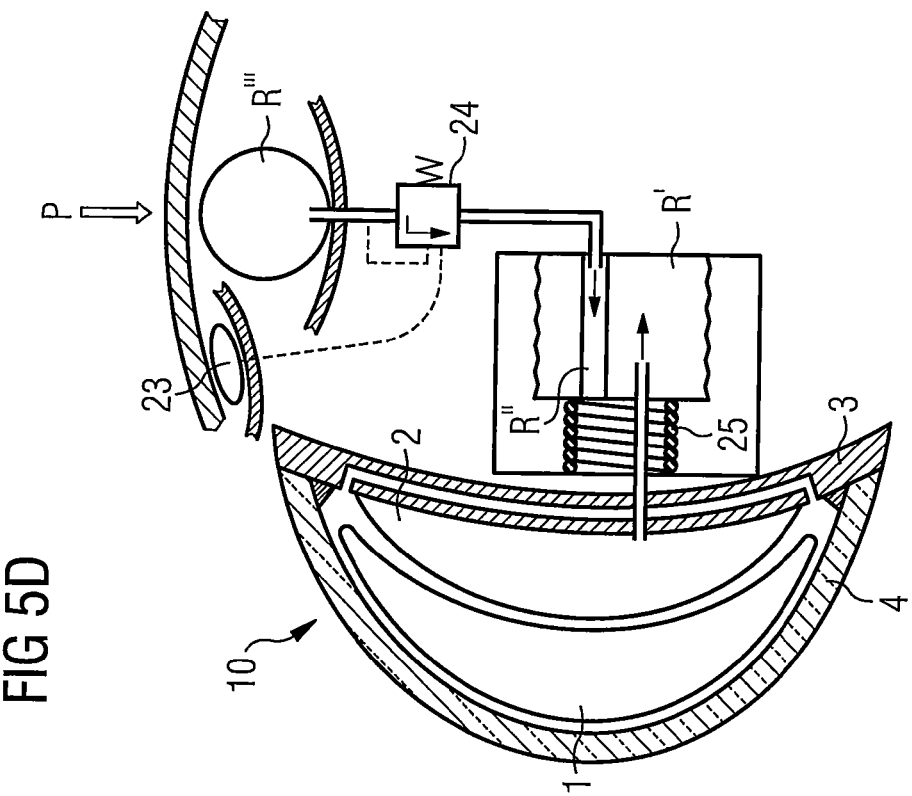
Figure 5D:
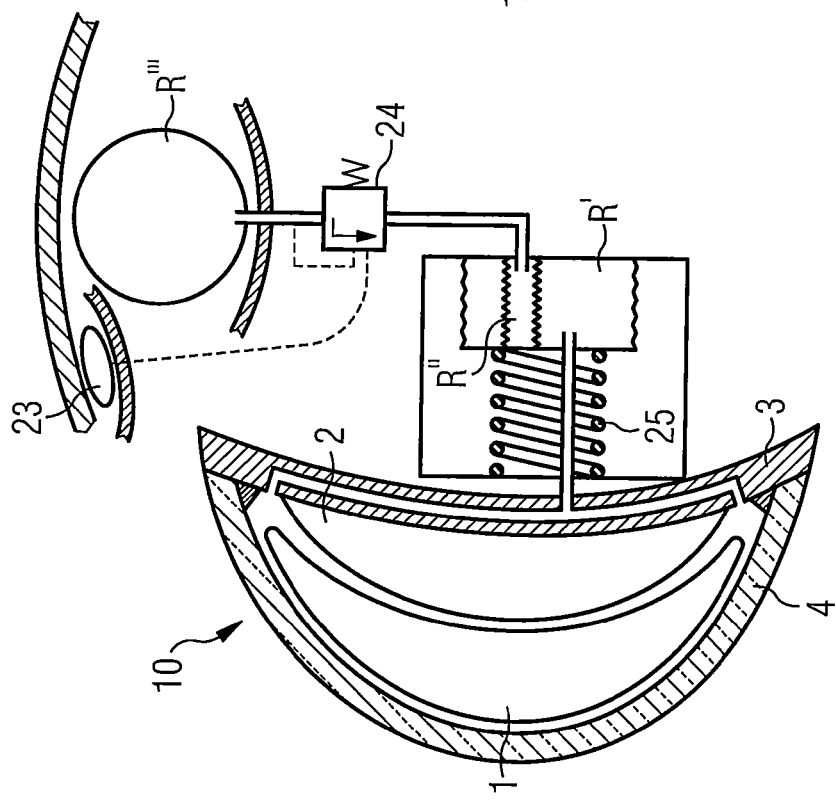

In this situation, the freely movable first element 1 can be displaced from a spot beside or, in the perspective shown, partly underneath the second element 2 to a different spot, such as on top of the second element 2 as shown in FIG. 5C, so as to change the outer shape of the breast implant 10 from relatively flat to relatively high. Once the relocation of the first element 1 has resulted in an appropriate shape change of the breast implant 10, the lubricating fluid has to be removed from the casing 3, 4 again. Accordingly, the patient can simply compress the subcutaneously implanted third sub-chamber R''' of the lubricating fluid reservoir, as is indicated in FIG. 5D by arrow P. The increased pressure in the third sub-chamber R''' will cause the valve 24, which is designed as a pressure relief valve, to open so that fluid flows from the third sub-chamber R''' into the second sub-chamber R''. The second sub-chamber R'' will expand accordingly against the force of the spring 25 and, thus, compress the spring 25 so that it assumes again its initial position as in FIG. 5A. This will in turn cause the first sub-chamber R' to expand also, and the lubricating fluid will be drawn from the casing 3, 4 of the breast implant 10 back into the remotely implanted first sub-chamber R' of the servo system. The subcutaneously implanted third sub-chamber R''' thus functions as a manually operable pump.

With the servo system shown in FIGS. 5A to 5D, the subcutaneously implanted third sub-chamber R''' can be kept relatively small so that it will not disturb the patient's appearance too much. For instance, it can advantageously be placed under the patient's arm. As a negative side effect, the pressure that the patient has to apply to the third sub-chamber R''' in order to overcome the force of the spring 25 is relatively high. However, if the spring load is kept small, this has the effect that the supply of lubricating fluid into the casing 3, 4 of the breast implant 10 by automatic action of the spring 25 takes somewhat longer.

It should be noted that subcutaneously implanted pressure chamber 23 for actuation of valve 24 can be replaced with automatic components such as a switch and an electric motor. Likewise, instead of manually compressing the third sub-chamber R''', a pump and a motor driving the pump may be used, possibly activated by means of a subcutaneously implanted pressure switch.

In addition to the lubricating fluid reservoir R (possibly even without a servo system, i.e. not separated in sub-chambers R' to R'''), the breast implant system may comprise a further reservoir and/or pump connected to the first and second elements 1, 2 in order to remove fluid from one element and supply an equivalent amount of fluid to the respective other element. This is shown in FIGS. 5E and 5F, which may be understood as showing a different cross section of the breast implant 10 of FIGS. 5A to 5D without the lubricating fluid reservoir and its associated servo system. Thus, in addition to relocating the first element 1 within the casing 3, 4 (or possibly more than only one such element) so as to change the shape of the breast implant, the shape can further be changed by inter-exchanging fluid between the elements 1 and 2, here by interaction of an intermediate pump 6, 7, similar to FIG. 1A or 4A, 4B. The volume of the breast implant 10, however, remains unaffected by such shape change. Nevertheless, the combination of relocating elements within the casing 3, 4 and inter-exchanging fluid among some or all of the elements 1, 2 within the casing 3, 4 offers a great variety of possibilities for adapting the shape of the breast implant 10. In any case, once the desired shape has been obtained, the lubricating fluid is withdrawn from the casing 3, 4 back into the reservoir R.

FIGS. 6A and 6B likewise show a breast implant 10 according to a sixth embodiment with a first cushion-like or pad-like element 1 and a second cushion-like or pad-like element 2 accommodated in a casing 3, 4, similar to FIGS. 5A and 5B. The lubricating fluid reservoir R connected to the interior of the casing 3, 4 may or may not involve a servo system as explained in relation to FIGS. 5A to 5D. The difference as compared to the embodiment shown in FIGS. 5E, 5F lies in the fact that fluid cannot be inter-exchanged between the first and second elements 1, 2, neither directly (such as described in relation to FIGS. 2A to 2C) nor via a pump (such as the pump 6, 7 in FIGS. 5E, 5F). Rather is a separate fluid reservoir $R_1$ and $R_2$ associated to each of the first and second elements 1, 2. As can be seen from a comparison of FIGS. 5E, 5F with FIGS. 6A, 6B, the same shape change of the breast implant 10 from relatively flat to relatively high can be achieved. However, the embodiment shown in FIGS. 6A to 6B offers further options for changing not only the shape but also the size of the breast implant 10, in that reservoirs $R_1$ and $R_2$ can be individually filled and emptied in order to individually deflate and inflate the associated first and second elements 1, 2.

Instead of being entirely freely movable within the casing 3, 4, the first element 1 may be partly connected to the casing, e.g. to the wall 4, and/or to the second element 2 in order to limit the boundaries of movement thereof. For instance elements 1 and 2 may be interconnected so that the fluid line from the first element 1 to the reservoir $R_1$ passes through the second element 2. Likewise, a valve such as the pressure relief valve 12 from FIGS. 2A to 2C may be present in the connecting area, or the connecting area may be completely closed. The connection may also comprise one or more straps by which the first element 1 is bound to neighboring surfaces.

FIGS. 7A to 7D show a seventh embodiment similar to the fifth embodiment, however, with the sole difference that the elements 1 contained in the casing 3, 4 are not cushion-like or pad-like but are much smaller and may have the form of little balls. There may be hundreds of balls 1 contained in the casing 3, 4, and these balls are preferably not fully inflated but have a slack wall so as to provide large contacting surfaces between adjacent balls 1. However, it is likewise possible that the elements 1 are made of fine granular and/or rigid material. In any case, it should be understood that FIGS. 7A and 7B only schematically show the principle that a great number of such elements 1 are contained in the casing 3, 4. While FIGS. 7A to 7D show the elements as being spaced apart, they are in fact not spaced apart but completely fill the interior of the casing 3, 4, as their purpose is to define the outer shape of the overall breast implant 10.

Figure 7D:
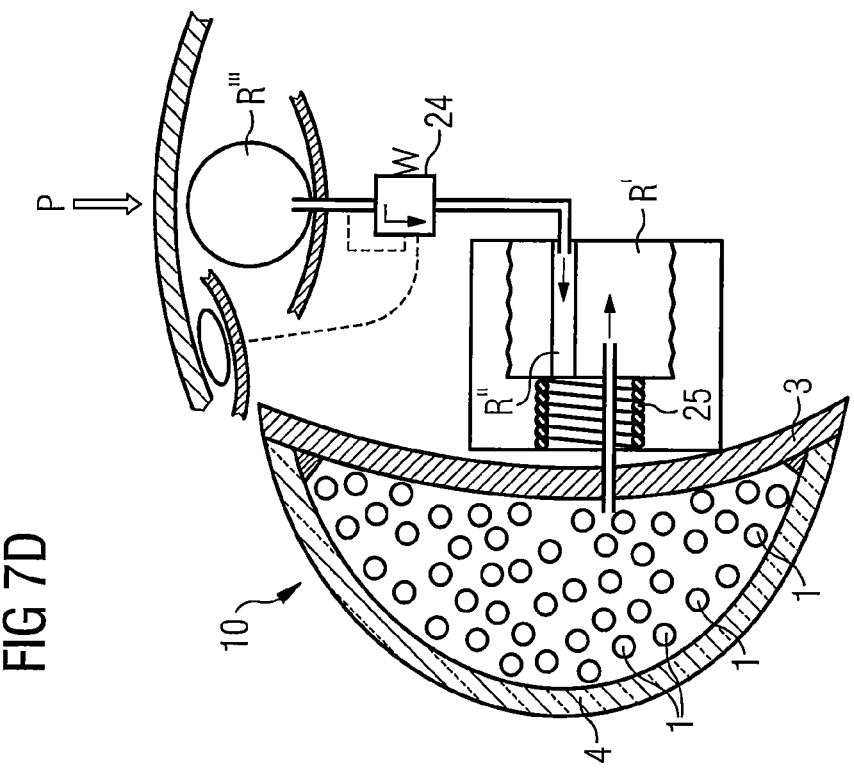
Figure 7C:
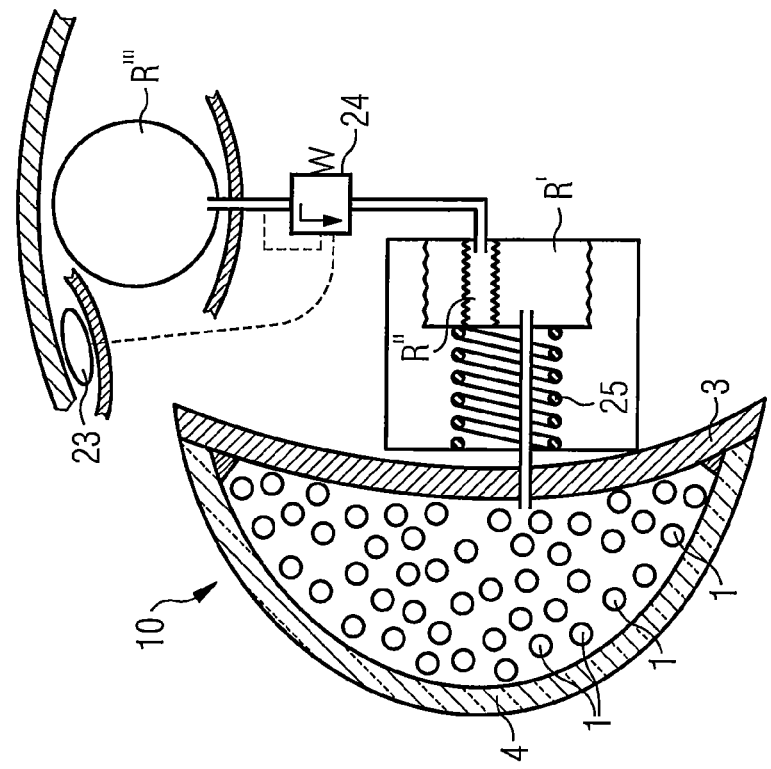

FIG. 7A shows an initial state in which the breast implant 10 is relatively flat and the lubricating fluid is still contained in the first sub-chamber R' of the lubricating fluid reservoir. When a shape change is desired, lubricating fluid is first supplied from the first sub-chamber R' into the casing 3, 4 using the servo system, as shown in FIG. 7B. Surface friction between the elements 1 contained in the casing 3, 4 is accordingly reduced. This allows for manual manipulation of the breast implant 10 to achieve a different shape of the breast implant 10, which may be relatively high as shown in FIG. 7C. When satisfied with the achieved shape change, the lubricating fluid is withdrawn from the casing 3, 4 by compressing the third sub-chamber R''' of the lubricating fluid reservoir, as indicated in FIG. 7D by arrow P. In the absence of the lubricating fluid, the surface friction among the elements 1 contained in the casing 3, 4 substantially increases so that the change of the shape is maintained over long time.

A servo system similar to the one shown in FIGS. 7A to 7D may also be used in context with the fluid reservoirs $R_1$ and $R_2$ in FIGS. 6A, 6B or any other reservoir for inflating and deflating one or more of the elements 1, 2 contained in the casing 3, 4.

Figure 8B:
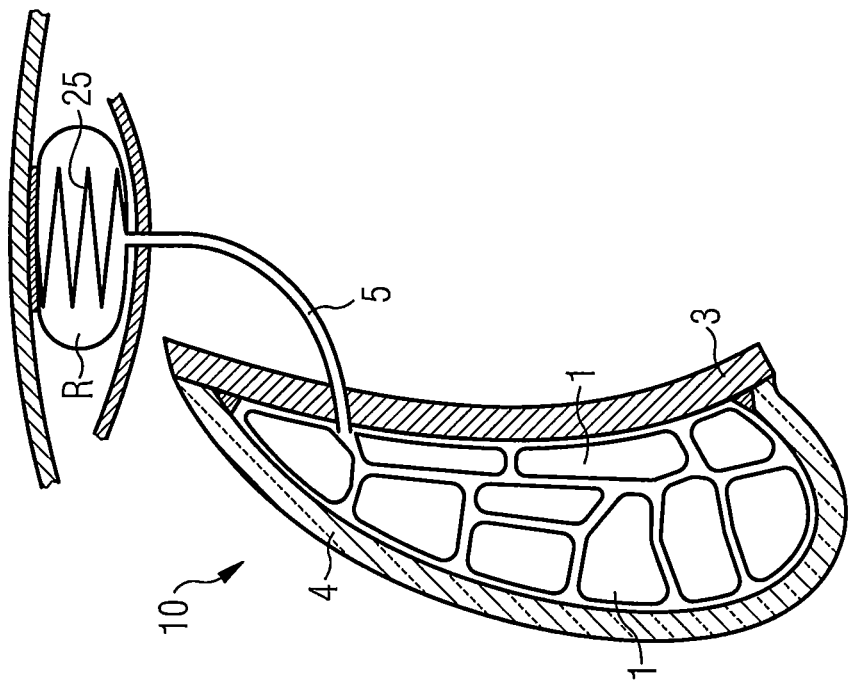
FIGS. 8A-8B show a breast implant system according to an eighth embodiment of the present invention.
Figure 8A:
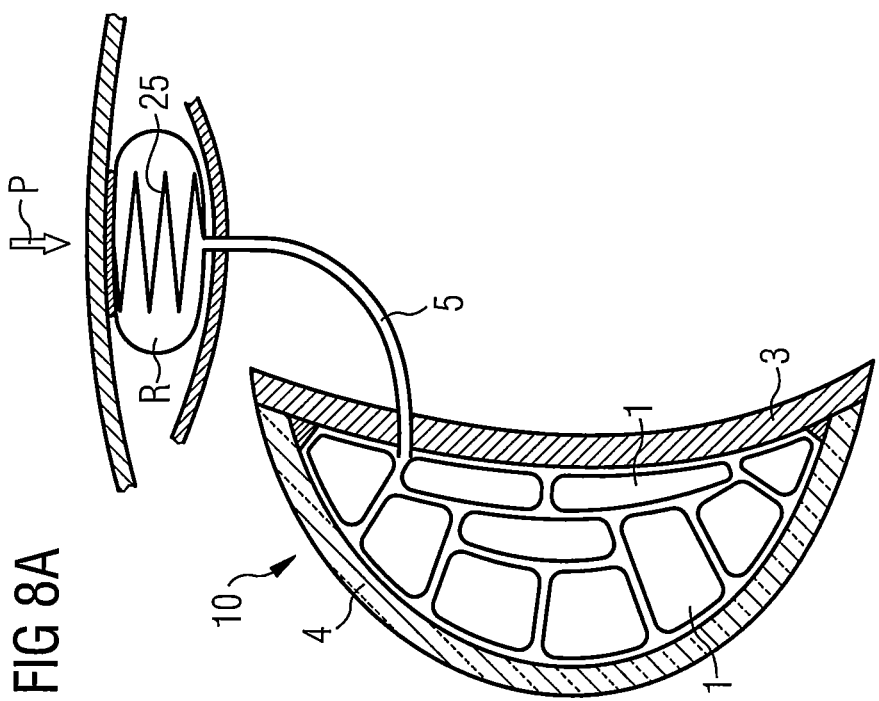

FIGS. 8A and 8B show an eighth embodiment with a purely subcutaneously arranged lubricating fluid reservoir R, shown in FIG. 8A in a non-operated state. The reservoir R is fully expanded due to the force of a compressing spring 25 contained in the reservoir. Thus, the lubricating fluid reservoir R may be e.g. of balloon-type or bellows-type. When a shape change is desired, the lubricating fluid reservoir R is compressed from outside the patient's body, as indicated in FIG. 8A by arrow P. The system with the reservoir R being compressed is not specifically shown in FIGS. 8A, 8B. However, once the lubricating fluid has been supplied from the reservoir R into the casing 3, 4 by e.g. the patient's left hand, surface friction between the elements 1 is accordingly reduced and the shape of the breast implant 10 can easily be manipulated manually using the right hand. Such manipulation will cause a relocation of the elements 1 between different spots within the casing 3, 4, which in turn causes the outer shape of the breast implant 10 to change from relatively high in FIG. 8A to relatively flat in FIG. 8B, or vice versa. Once the desired shape is achieved, the pressure P on the reservoir R is released and the elastic force of the spring 25 causes the lubricating fluid to be withdrawn from the casing 3, 4 back into the reservoir R.

The elements 1 in the embodiment shown in FIGS. 8A, 8B are substantially smaller than the cushion-like elements and are substantially larger than the ball-like elements in the previous embodiments. At least some of them may be interconnected so as to limit there relative movement and/or at least some of them may be connected to the casing so as to at least limit their movement in respect of the wall 4 or the back plate 3 of the casing 3, 4. Also, at least some of the elements 1 may be interconnected so as to allow for interexchanging fluid directly, or may be connected to one or more remotely implanted reservoirs via associated fluid conduits. Such fluid reservoirs may likewise be implanted subcutaneously for manual operation in the manner of a pump. All these options are not specifically shown in FIGS. 8A and 8B, and it is evident that these options are likewise applicable to the breast implant independent of the particular realization of the lubricating fluid reservoir R.

FIGS. 9A to 9B show a ninth embodiment of how lubricating fluid can be supplied to and removed from the interior of the casing 3, 4, which casing is displayed very schematically in FIGS. 9A, 9B. For reason of simplification, the elements filling the casing 3, 4 are not shown in FIGS. 9A, 9B. The lubricating fluid reservoir R is again adapted for subcutaneous implantation here. First, pressure P is exerted on the reservoir R from outside the patient's body so as to urge fluid to flow through a two-way non-return valve 28 and through line 5 into the casing 3, 4 (FIG. 9A). The two-way non-return valve 28 placed in line 5 connecting the reservoir R with the casing 3, 4 is schematically shown in more detail in FIG. 9C. The form of the breast implant 10 can then be reshaped easily, e.g. by manual manipulation from outside the breast implant 10 or using automatic components, such as implanted elements including pump, motor and the like. After reshaping is completed (FIG. 9B), pressure can be applied on the casing 3, 4 from outside the breast implant 10 as uniformly as possible so as to avoid further rearrangement of the elements within the casing. Thus, upon manual compression of the breast implant 10, as indicated by arrows P in FIG. 9B, the lubricating fluid in the casing 3, 4 is urged back through valve 28 into the remotely implanted reservoir R.

Figure 10:
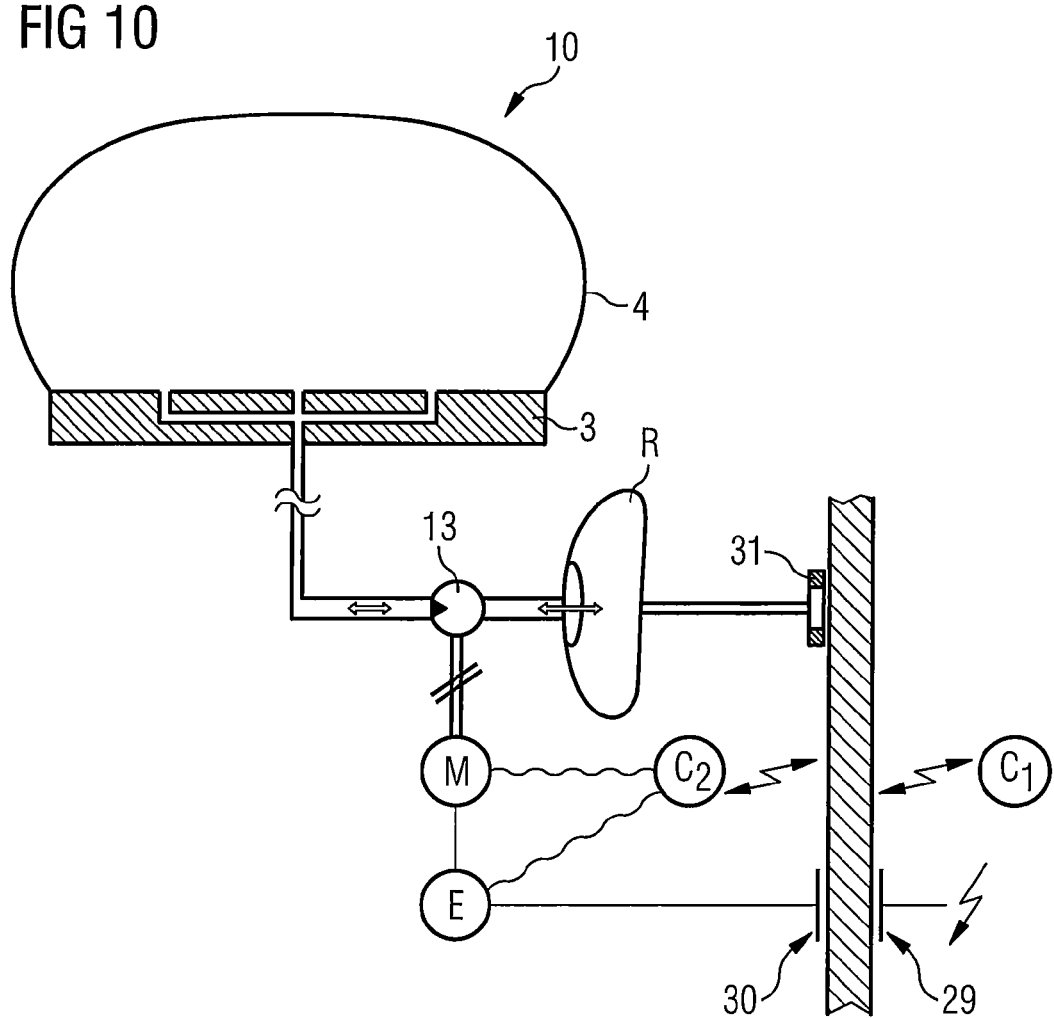
FIG. 10 shows a breast implant system according to a tenth embodiment of the present invention.

FIG. 10 shows a tenth embodiment of a more complex breast implant system. The basic structure of the breast implant system corresponds to the structure described above in relation to FIGS. 9A and 9B, but could also be completely different. What is important in the embodiment shown in FIG. 10 is a pump P driven by a motor M and arranged to pump fluid between the reservoir R and the casing 3, 4. The reservoir R may be implanted anywhere convenient in the patient's body, such as in the abdominal cavity.

The motor M is energized with wirelessly transmitted energy. For this purpose, the breast implant system comprises an energy transmitter 29 outside the patient's body and an energy transforming device 30 inside the patient's body, preferably subcutaneously implanted, to transform the wireless energy into electric energy. While it is possible to make use of a motor M adapted to directly transform the wirelessly transmitted energy in kinetic energy, or, alternatively, to use the wirelessly transmitted energy transformed into electric energy by means of the energy transforming device 30 to drive the motor M as the energy transforming device transforms the wireless energy into the electric energy, the specific embodiment shown in FIG. 10 first stores the transformed electric energy in an energy storage means E, before it is supplied to the motor M. Of course, it is also possible that a part of the transformed electric energy is directly used by the motor while another part of the transformed electric energy is stored in the energy storage means E. The energy storage means E may include at least one accumulator such as a rechargeable battery and/or a capacitor. It is less convenient, but possible, to implant a regular battery as the energy storage means E. But a regular battery may be used as the energy source to provide the wireless energy to be transmitted from outside the patient's body.

The breast implant system shown in the specific embodiment of FIG. 10 further includes a control unit. The control unit here comprises a first part C1 to be used by the patient from outside the patient's body and a second part C2 to be implanted inside the patient's body. Data can thus be transmitted wirelessly between the first and second parts C1, C2 of the control unit. In addition or alternatively, the implantable second part C2 of the control unit may be programmable via the first part of the control unit. Preferably, the data are transmitted between the first and second parts C1, C2 of the control unit in the same manner as energy is transmitted, such as via the elements 29 and 30.

The external part C1 of the control unit may also be replaced with a simple manually operable switch for activating the implantable control unit C2. Such switch is then arranged for subcutaneous implantation so as to be operable from outside the patient's body. It is also possible to combine the switch with an external part C1 of the control unit.

Furthermore, feedback information may be sent between the implanted part C2 and the external part C1 of the control unit. Such feedback information may include information related to the energy to be stored in the energy storage means E. The control unit can make use of such feedback information for adjusting the amount of wireless energy transmitted by the energy transmitter 29. The feedback information may be related to an energy balance, which may be defined either as the balance between an amount of wireless energy received inside the human body and an amount of energy consumed by the motor and pump, or as the balance between a rate of wireless energy received inside the human body and a rate of energy consumed by the motor and pump.

FIG. 10 further shows an injection port 31 implanted under the patient's skin. Fluid can be added to or removed from the breast implant system through the injection port 31 by means of a regular syringe if need arises.

Clearly, a system like the one described in relation to FIG. 10 can also be used to inflate and deflate one or more of the elements (not shown) contained in the casing 3, 4.

In context with an eleventh embodiment of a breast implant system, FIGS. 11A to 11D show a manner of implanting the lubricating fluid reservoir R remote from the breast implant next to the thorax under the pectoralis muscle. The casing of the breast implant 10 is here formed solely from the flexible wall 4 within which a great number of elements is contained, such as the previously described small balls. However, the breast implant 10 may also take any other form and configuration. It is designed to increase the volume of a natural breast 50, but can likewise be designed to replace an amputated breast. A pump 5 is also implanted remote from the breast implant 10 to exchange fluid between the casing and the reservoir R. The pump 5 may be combined with a motor, control unit, and other parts of the system previously described. Instead of or in addition to the pump 5, other elements of the breast implant systems described before may be combined with this eleventh embodiment, such as remotely implanted components for manual operation by the patient, pressure relief valves and so forth.

Figure 11A:
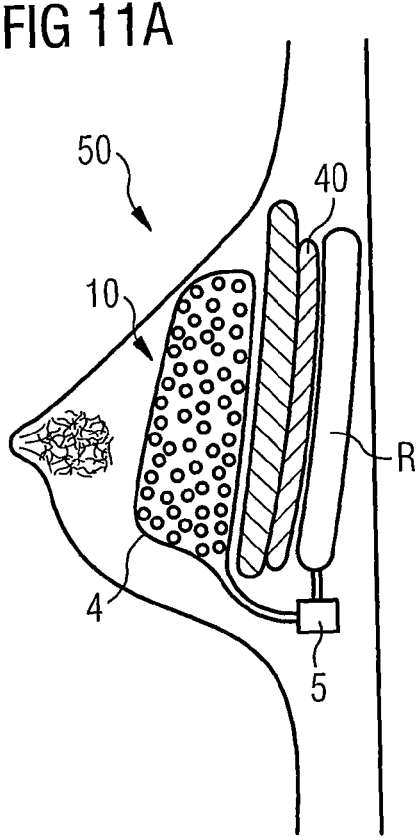
Figure 11B:
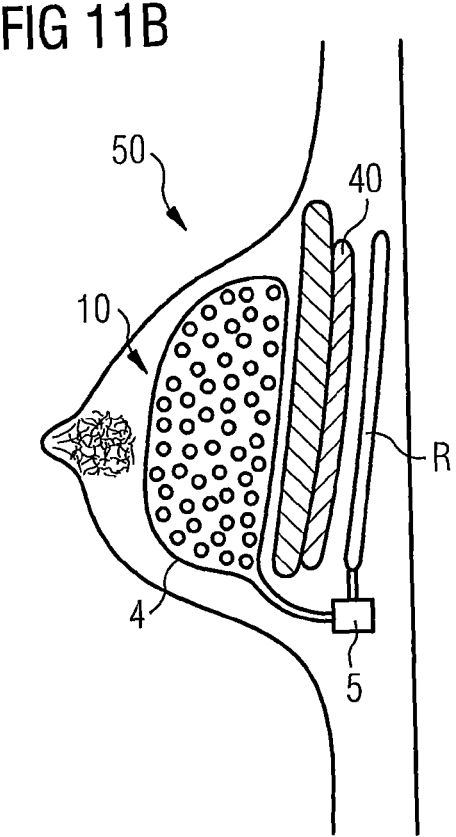
Figure 11C:
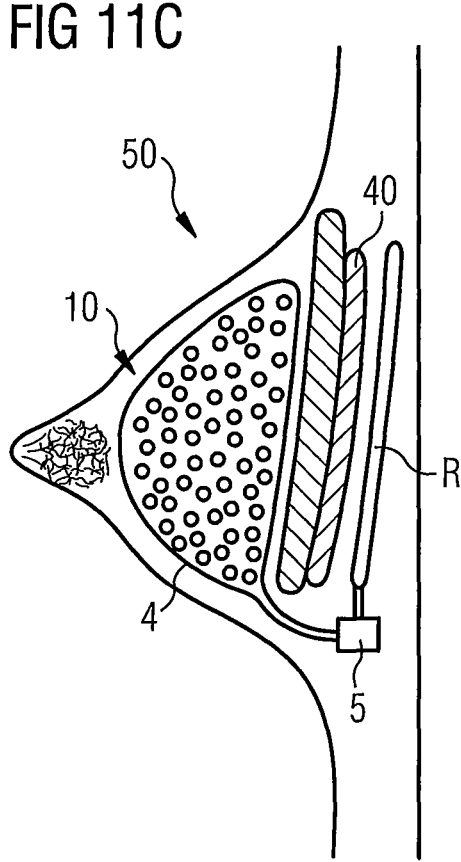
Figure 11D:
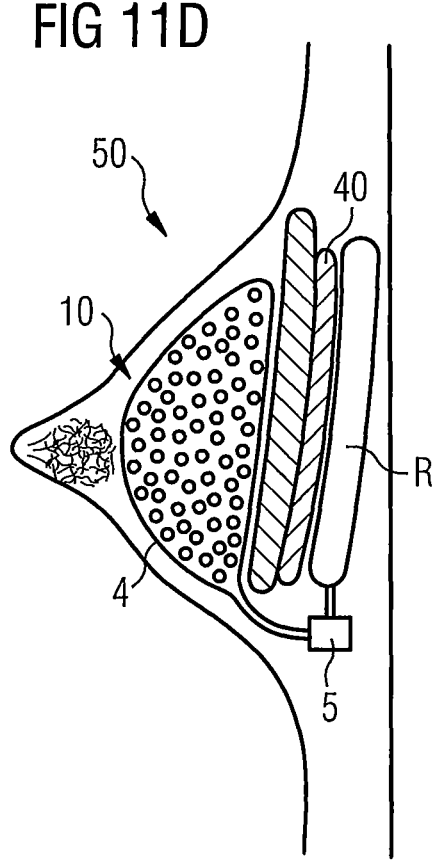

FIGS. 11A to 11D show the sequence of changing the shape of the breast implant 10. FIG. 11A shows an initial state with the breast 50 being neither flat nor high. FIG. 11B shows an intermediate state with the lubricating fluid from reservoir R being pumped into the casing using the pump 5. Surface friction among the elements contained in the casing is accordingly reduced and permits easy reshaping of the breast implant 10 by manual manipulation. A possible result of the reshaping is shown in FIG. 11C. Once the desired shape has been achieved, pump 5 is used to withdraw the lubricating fluid from the casing back into the reservoir R, as shown in FIG. 11D. Surface friction among the elements contained in the casing is accordingly increased again so as to maintain the new shape of the breast implant 10.

Instead of implanting the reservoir R under the minor pectoralis muscle, it may likewise be placed between the patient's minor pectoralis muscle 40 and major pectoralis muscle 41, as is shown in FIG. 12. This arrangement may be more convenient for the patient.

It should be understood that not only the lubricating fluid reservoir R but also the further reservoir, if present, for changing the fluid content within one or more of the elements contained in the casing can be placed under the minor pectoralis muscle or between the minor and major pectoralis muscles either along with the lubricating fluid reservoir R or separate thereto.

The invention claimed is:

1. A breast implant system comprising:
    at least one casing with a flexible outer shape for permanent implantation in a patient's body so as to form part of a breast implant,
    at least one first element contained in the casing, and
    a reservoir adapted to be implanted and filled with a lubricating fluid, the reservoir being connected to the casing so as to allow the lubricating fluid to be supplied from the reservoir to the casing between an outer surface of said at least one first element contained in the casing and surfaces contacting said outer surface in order to reduce surface friction between the outer surface of said at least one first element and the surfaces contacting said outer surface, and wherein the breast implant system is adapted to allow the lubricating fluid to be at least partly removed from the casing back into the reservoir.

2. The breast implant system of claim 1, adapted to change the friction between surfaces in the breast implant to allow a change of the outer shape of the breast implant post-operatively.

3. The breast implant system of claim 2, adapted to change the friction between surfaces in the breast implant to allow a change of the outer shape of the breast implant non-invasively.

4. The breast implant system of claim 1, wherein the outer surface of the at least one first element or of at least two or at least three first elements is displaceable relative to a contacting inner surface of the casing or relative to a contacting outer surface of the at least one second element or relative to both a contacting inner surface of the casing and a contacting outer surface of the at least one second element.

5. The breast implant system of claim 1, wherein the reservoir is adapted for implantation inside the patient's chest area outside the thorax either below the minor pectoralis muscle or between the major and the minor pectoralis muscles.

6. The breast implant system of claim 1, wherein the reservoir is adapted for implantation within the patient's body remote from the breast implant, the system further comprising at least one conduit between the remotely implantable reservoir and the casing for fluid exchange between the reservoir and the casing.

7. The breast implant system of claim 6, wherein at least a part of the reservoir is adapted to be implanted in the armpit or underneath the patient's arm or in the patient's abdominal cavity.

8. The breast implant system of claim 6, wherein at least a part of the reservoir is adapted to be implanted subcutaneously such that fluid can be exchanged between the casing and the reservoir by manually compressing the subcutaneously implanted reservoir or part thereof, thereby urging fluid to flow from the reservoir into the casing.

9. The breast implant system of claim 1, comprising at least one valve between the reservoir and the casing.

10. The breast implant system of claim 9, wherein the at least one valve includes a pressure relief valve which opens in at least one direction at a predetermined pressure.

11. The breast implant system of claim 1, comprising 10 or more of the first elements contained in the casing.

12. The breast implant system of claim 11, comprising 100 or more of the first elements contained in the casing.

13. The breast implant system of claim 1, wherein the outer wall of the casing has a shape adapted to allow lengthening of the functional length thereof without interfering with fibrosis covering said outer wall, when the breast implant is implanted in the body.

14. The breast implant system of claim 13, wherein the outer wall has at least one wrinkle or crease adapted to allow lengthening of the outer wall without lengthening fibrosis covering the outer wall when implanted.

15. The breast implant system of claim 1, wherein at least one first element and at least one second element within the casing are interconnected so as to allow for exchanging content between them.

16. The breast implant system of claim 1, wherein the outer surface of the at least one first element is displaceable relative to a contacting outer surface of the at least one second element by moving the first element between different spots within the casing so as to change the outer shape of the breast implant.

17. The breast implant system of claim 1, wherein the exchange of an amount of fluid between the reservoir and the casing involves a displacement of an amount of fluid between sub-chambers of the reservoir, said amount of fluid displaced between sub-chambers of the reservoir being different to the amount of fluid exchanged between the casing and the reservoir.

18. The breast implant system of claim 1, further comprising at least one pump adapted for exchanging lubricating fluid between the reservoir and the casing or adapted for pumping fluid between the first and second elements.

19. The breast implant system of claim 18, further comprising at least one motor arranged for automatically driving the pump.

20. The breast implant system of claim 1, further comprising an energy source for supplying energy directly or indirectly to at least one energy consuming part of the system, wherein said energy source includes an energy storage means adapted for being implanted inside the patient's body.

21. The breast implant system of claim 18, further comprising a control unit adapted to directly or indirectly control the at least one pump or another component of the system.

22. The breast implant system of claim 21, wherein the control unit is adapted to be operable by the patient from outside the patient's body.

* * * * *